(12) United States Patent
Ryan et al.

(10) Patent No.: US 6,793,635 B2
(45) Date of Patent: Sep. 21, 2004

(54) DEVICES HAVING DEPLOYABLE ULTRASOUND TRANSDUCERS AND METHOD OF USE OF SAME

(75) Inventors: Thomas P. Ryan, Flemington, NJ (US); Alexander J. Sinton, Doylestown, PA (US)

(73) Assignee: Ethicon, Inc., Somerville, NJ (US)

( * ) Notice: Subject to any disclaimer, the term of this patent is extended or adjusted under 35 U.S.C. 154(b) by 99 days.

(21) Appl. No.: 10/187,276

(22) Filed: Jun. 28, 2002

(65) Prior Publication Data

US 2004/0002701 A1 Jan. 1, 2004

(51) Int. Cl.[7] .................................................. A61I 1/00
(52) U.S. Cl. ............................................. 601/2; 606/28
(58) Field of Search ................. 601/2–3; 606/27–28; 607/101, 102

(56) References Cited

U.S. PATENT DOCUMENTS

| | | | |
|---|---|---|---|
| 5,437,629 A | 8/1995 | Goldrath | |
| 5,620,479 A | 4/1997 | Diederich | |
| 5,733,315 A | 3/1998 | Burdette et al. | |
| 5,769,880 A | 6/1998 | Truckai et al. | |
| 5,853,368 A | * 12/1998 | Solomon et al. | 600/439 |
| 6,066,139 A | 5/2000 | Ryan et al. | |
| 6,595,989 B1 | 7/2003 | Schaer | |
| 6,645,202 B1 | * 11/2003 | Pless et al. | 606/41 |

OTHER PUBLICATIONS

Neuwirth, et al, "The Endometrial Ablator: A New Instrument", Obst. & Gyn., 1994, vol. 83, No. 5, Part 1, 792–796.
Prior, et al., "Treatment of Mennorrhagia By Radiofrequency Heating", Int. J. Hyperthermia, 1991 vol. 7, No. 2, 213–220.

* cited by examiner

Primary Examiner—Roy D. Gibson

(57) ABSTRACT

A device for thermal ablation therapy having emitting means for emitting ultrasound energy capable of heating tissue and moving means for moving the emitting means between an undeployed position, in which the emitting means is in a first orientation which facilitates insertion of the device, and a deployed position, in which the emitting means is in a different second orientation that is selected to efficiently deliver ultrasound energy to the tissue to be ablated. The moving means includes one or more movable carriers and the emitting means is one or more piezoelectric transducers that are securely mounted on the carriers for conjoint movement therewith. A method for thermal ablation therapy using ultrasound energy involves positioning an ultrasound device in an undeployed position proximate to tissue to be heated; moving the ultrasound device from its undeployed position to a deployed position; and activating the ultrasound device to emit ultrasound energy for a predetermined period of time.

16 Claims, 14 Drawing Sheets

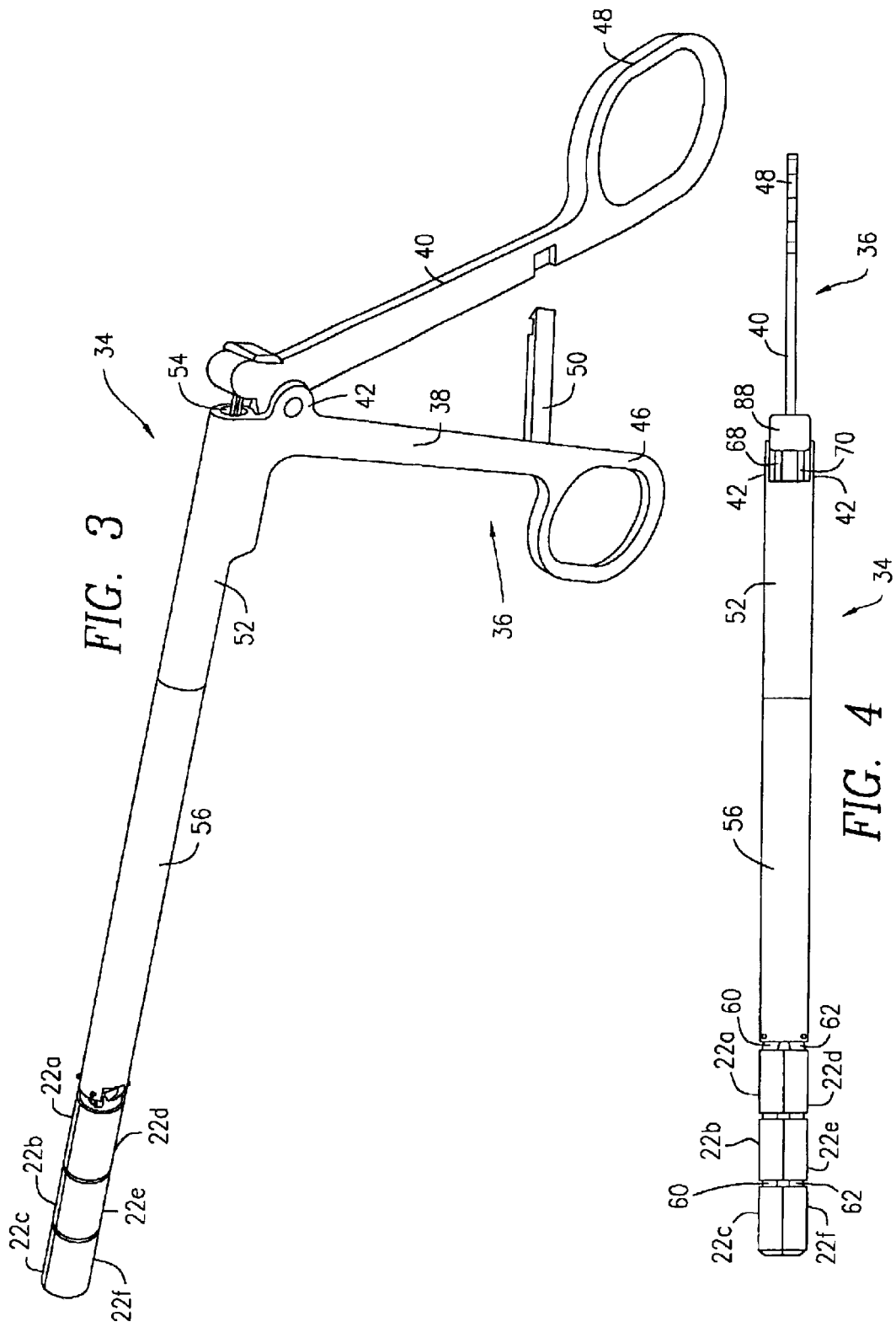

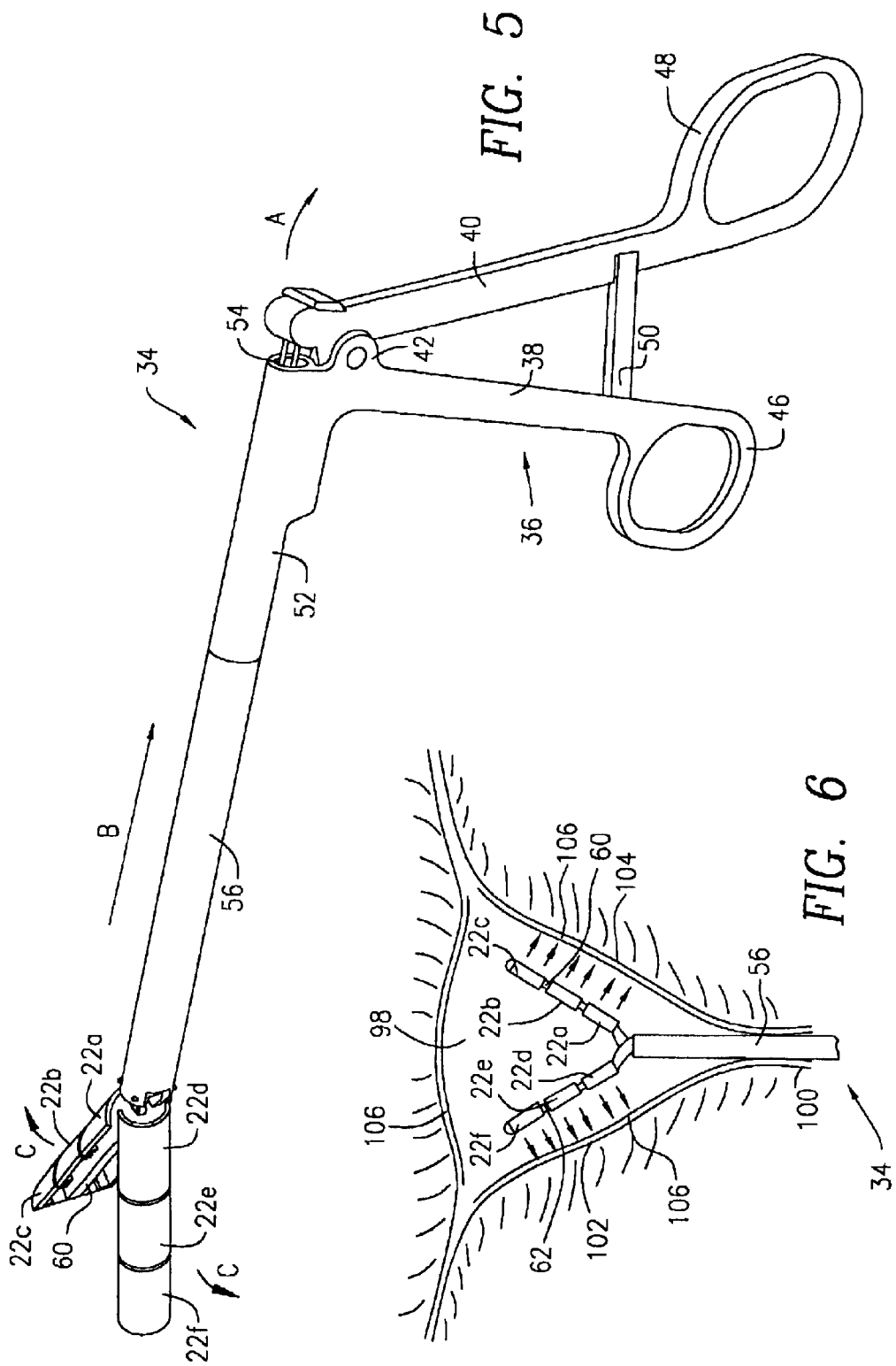

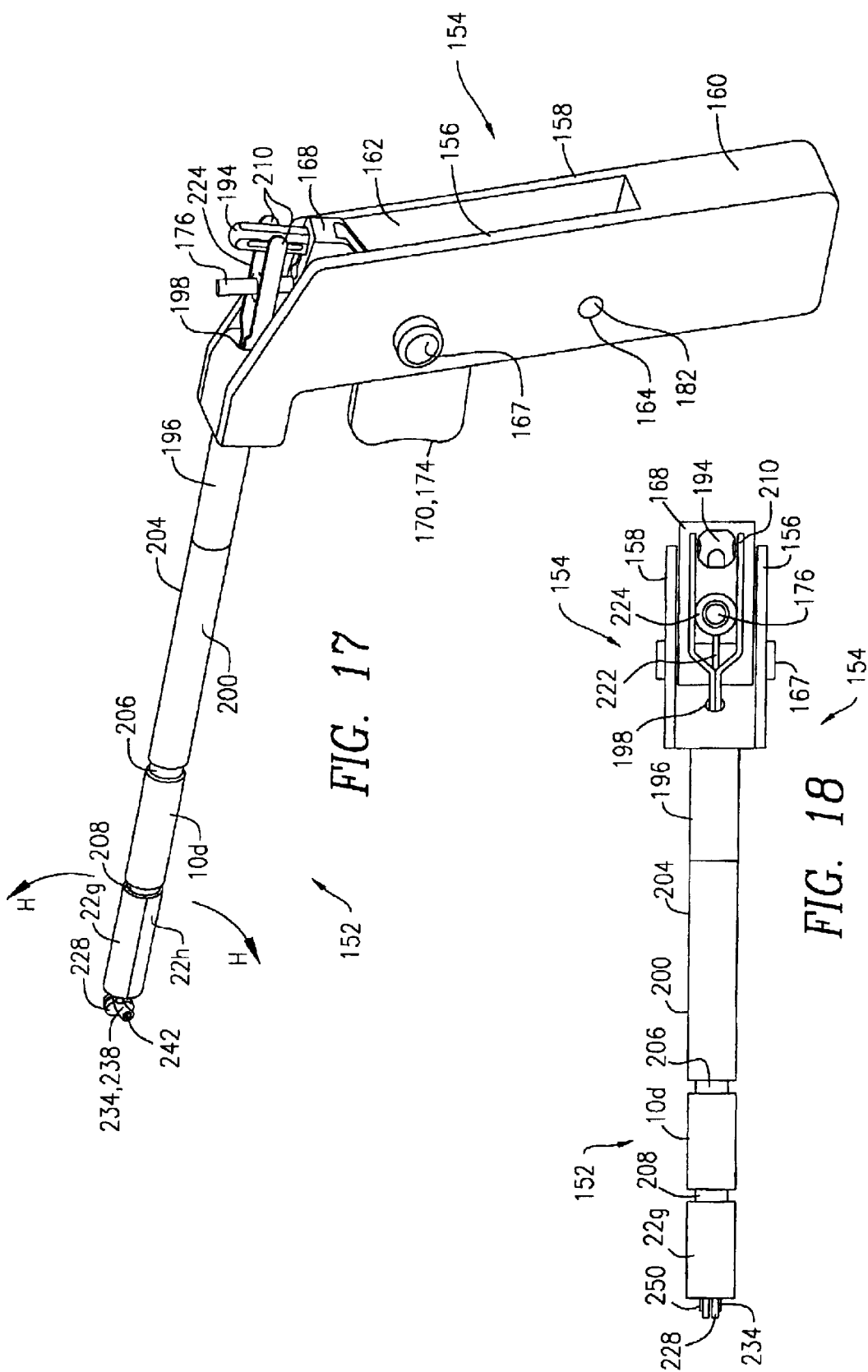

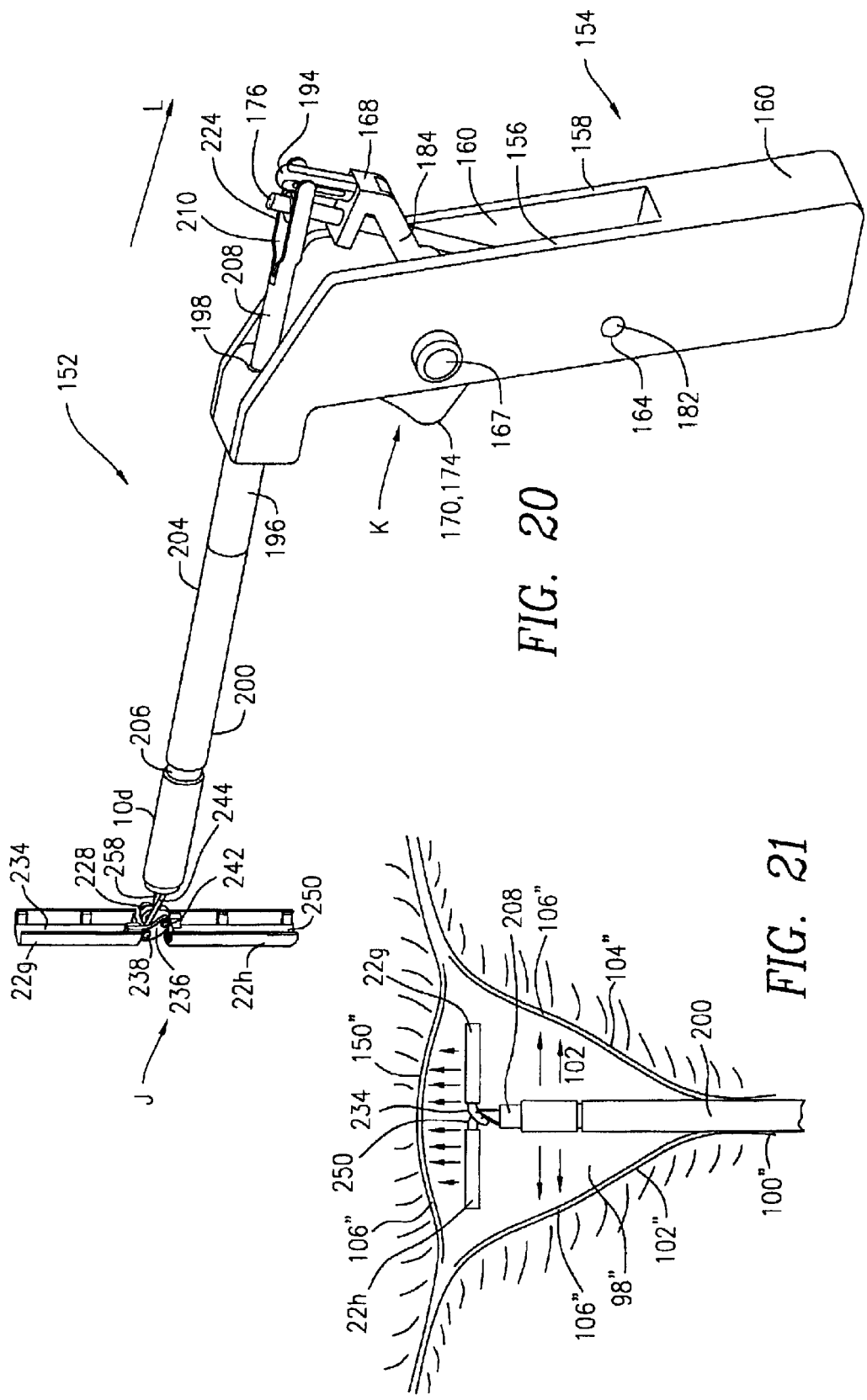

DEVICES HAVING DEPLOYABLE ULTRASOUND TRANSDUCERS AND METHOD OF USE OF SAME

FIELD OF THE INVENTION

The present invention relates to devices having deployable ultrasound transducers for performing endometrial ablation.

BACKGROUND OF THE INVENTION

Menorrhagia is a common problem in women that is characterized by extended or irregular menstrual cycles or excessive amounts of bleeding during menstrual cycles. The endometrium is the uterine lining which is responsible for the bleeding that occurs during menstrual cycles, as well as dysfunctional uterine bleeding. Heating to at least superficially destroy the endometrium, also known as endometrial ablation, has been shown to reduce the aforesaid abnormal bleeding. In some cases ablating the endometrium results in cessation of the menstrual bleeding altogether, which may be preferable to the irregular cycles and excessive bleeding that otherwise occur.

There are many technologies on the market and in clinical trials which utilize a range of energy sources, but the goal for each is the same, i.e., endometrial tissue destruction by thermal cryo-coagulation. For example, Neuwirth, et al, "The Endometrial Ablator: A New Instrument", Obst. & Gyn., 1994, Vol. 83, No. 5, Part 1, 792–796, performed endometrial ablation using a dextrose-filled balloon device mounted at the end of a carrier catheter and including a heating element inside the balloon. This device also includes a system that monitors the pressure and temperature inside the balloon. Neuwirth, et al. determined that if the surface of the balloon-tissue interface is maintained at about 90° C. for 7–12 minutes, the depth of damage to the endometrium was about 4–10 millimeters. This depth of damage is believed to be clinically acceptable to the extent that such a procedure could be considered as an alternative to surgical procedures, such as hysterectomy.

High frequency, or radiofrequency (RF), energy has been used to ablate the endometrium as well as cryo-techniques. For example, Prior, et al., "Treatment of Mennorrhagia By Radiofrequency Heating", Int. J. Hyperthermia, 1991 Vol. 7, No. 2, 213–220, achieved a significant reduction in dysfunctional uterine bleeding using a device that includes a probe having a high frequency RF energy source that is inserted directly into the patient's uterus through the vagina and cervix. The energy source is an RF system having an electrode on the probe and a belt placed around the patient that serves as the return electrode. This RF system is operated at 27.12 MHz at a power of 550 Watts for about 20 minutes and achieves a deeper penetration than the Neuwirth, et al. device, which is an advantage over the Neuwirth, et al. device.

A system marketed under the tradename THERMACHOICE®, by Ethicon, Inc. of Somerville, N.J., is currently used to perform endometrial ablation and includes a latex balloon filled with a heated dextrose and water solution. The balloon is attached to the distal end of a catheter carrier and the device often delivers satisfactory results. Some patients, however, present a need for deeper and broader endometrial penetration during ablation.

U.S. Pat. No. 5,620,479 discloses a device for thermal treatment having an array of tubular piezoelectric transducers disposed on a semi-flexible tubular carrier for delivering ultrasound energy directly to tissue to be ablated. The transducers are covered with a sealant coating and there is an outer covering over the sealant coating. This device also includes thermocouple sensors embedded in the sealant coating over each transducer for continuous monitoring of the tissue-applicator interface temperatures for feedback control of the power delivered to the transducers.

U.S. Pat. No. 5,733,315 also discloses a device for ablating tissue using ultrasound energy, but is adapted specifically for insertion into the rectum for treating the prostate. This device includes one or more ultrasound transducers disposed at least partly about a support tube, each ultrasound transducer having inactivated portions for reducing ultrasound energy directed to the rectal wall. The transducers of this device are also enclosed in a sealant.

U.S. Pat. No. 5,437,629 discloses an apparatus and method for recirculating heated fluid in the uterus to perform endometrial ablation, without using a balloon. U.S. Pat. No. 5,769,880 discloses an apparatus and method for performing tissue ablation, including endometrial ablation, using bipolar RF energy. This device includes an electrode-carrying member mounted to the distal end of a shaft and an array of electrodes mounted to the surface of the electrode carrying member. A vacuum is utilized to draw out vapors, which are created when the tissue is ablated.

The foregoing devices and techniques are all either too complex or provide less than optimal results. In addition, they all deliver energy in a general manner, without the ability to control or direct the application of energy in situ to the tissue to be treated. It is further noted that there are no devices specifically adapted for endometrial ablation that use therapeutic ultrasound.

The device of the present invention addresses the shortcomings of the existing apparatus and process for endometrial ablation by providing a device that delivers ultrasound energy to the endometrial tissue in a controlled and efficient manner by having deployable piezoelectric transducers mounted on movable carriers that are deployed after insertion into the uterus.

SUMMARY OF THE INVENTION

A device for thermal ablation therapy having emitting means for emitting ultrasound energy capable of heating tissue and moving means for moving the emitting means between an undeployed position, in which the emitting means is in a first orientation which facilitates insertion of the device, and a deployed position, in which the emitting means is in a different second orientation that is selected to efficiently deliver ultrasound energy to the tissue to be ablated. The emitting means is movable from the undeployed position to any one of an infinite number of orientations for efficiently delivering ultrasound energy to the tissue. The moving means is one or more movable carriers and the emitting means is one or more piezoelectric transducers that are securely mounted on the carriers for conjoint movement therewith.

The moving means includes a rod which has a distal end and a proximal end, and a hollow sleeve, which has a through passage. The rod is slideably received in the through passage and the distal end of the rod is connected to a carrier, whereby sliding movement of the rod moves the piezoelectric transducer or transducers mounted thereon between the undeployed and deployed positions. The piezoelectric transducer and the sleeve are linearly arranged relative to each other when the piezoelectric transducer is in its undeployed position. When the piezoelectric transducer is in its deployed position, the piezoelectric transducer and the sleeve are arranged relative to each other in a non-linear manner. In addition, moving means may also include a handle having a movable part that is connected to the proximal end of the rod for moving the piezoelectric transducer between its undeployed and deployed positions in response to movement of the movable part of the handle.

In one embodiment, a set of first transducers is mounted linearly on a first carrier and a set of second transducers is mounted linearly on a second carrier. When the first and second transducers are in their undeployed positions, the first transducers are arranged linearly relative to the sleeve and the second transducers are also arranged linearly relative to the sleeve. When the first and second transducers are in their deployed positions, the first transducers are arranged at an angle relative to the sleeve and the second transducers are arranged at an angle relative to the sleeve and relative to said second transducers In another embodiment, a plurality of transducers are mounted linearly on a carrier. When the transducers are in their undeployed positions, they are arranged linearly relative to the sleeve and when the transducers are in their deployed positions, they are arranged perpendicularly relative to the sleeve.

In still another embodiment, a first carrier has a first transducer mounted thereon and a second carrier includes a second transducer mounted thereon and the first and second carriers are pivotable relative to one another such that the first and second transducers are movable between their undeployed and deployed positions. When the first and second transducers are in their undeployed positions the first and second transducers are both arranged linearly relative to the sleeve. When the first and second transducers are in their deployed positions, the first and second transducers are oriented substantially perpendicularly relative to the sleeve and the first and second transducers are arranged linearly relative to one another.

A method for thermal ablation therapy using ultrasound energy involves positioning an ultrasound device in an undeployed position in which said ultrasound device in is a first orientation which facilitates positioning of the device proximate to tissue to be heated; moving the ultrasound device from its undeployed position to a deployed position which is selected to efficiently deliver ultrasound energy to tissue to be heated; and activating the ultrasound device to emit ultrasound energy for a predetermined period of time.

BRIEF DESCRIPTION OF THE DRAWINGS

For a better understanding of the present invention, reference is made to the following detailed description of a preferred embodiment of the present invention considered in conjunction with the accompanying drawings, in which:

FIG. 3 is a perspective view of a first embodiment of the device of the present invention, in an undeployed state;

FIG. 4 is a top plan view of the first embodiment of the device of FIG. 3;

FIG. 5 is a perspective view of the first embodiment of the device of FIG. 3, in a deployed state;

FIG. 6 is a schematic cut away view of the first embodiment of the device of FIG. 5, in a delpoyed state, positioned within the uterus of a patient and showing, schematically, the direction of emission of ultrasound energy from the transducers;

FIG. 17 is a perspective view of a third embodiment of the device of the present invention, in an undeployed and extended state;

FIG. 18 is a top plan view of the third embodiment of the device of FIG. 17;

FIG. 20 is a perspective view of the third embodiment of the device of FIG. 17, in a deployed and retracted state;

FIG. 21 is a schematic cut away view of the first embodiment of the device of FIG. 20, in a delpoyed and retracted state, positioned within the uterus of a patient and showing, schematically, the direction of emission of ultrasound energy from the transducers;

DETAILED DESCRIPTION OF THE INVENTION

The three embodiments of the device of the present invention that are described hereinafter each employ piezoelectric transducers for producing and emitting ultrasound energy to ablate the endometrium of patients experiencing dysfunctional uterine bleeding. The basic construction and operation of piezoelectric transducers are well known and understood to those having ordinary skill in the art. However, in order to facilitate the description of the device present invention, the following discussion provides a general description of piezoelectric transducers of two particular shapes, i.e., cylindrical and hemi-cylindrical, that are most suitable for use with the preferred embodiments of the present invention. Both of these piezoelectric transducers are made of ceramic material such as, PZT4, PZT8, or C5800, each of which is commercially available from ValpeyFischer Corp, Hopkinton, Mass.

Figure 1A:
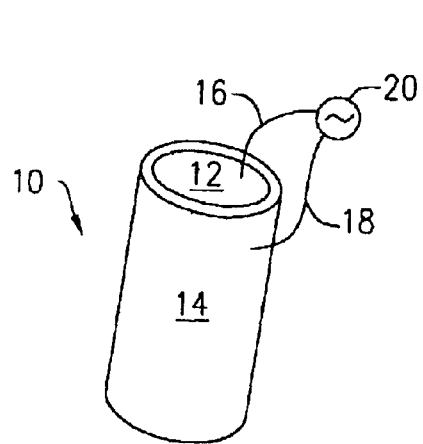
FIG. 1A is a schematic perspective view of a cylindrical piezoelectric transducer used in connection with certain embodiments of the present invention.
Figure 1B:
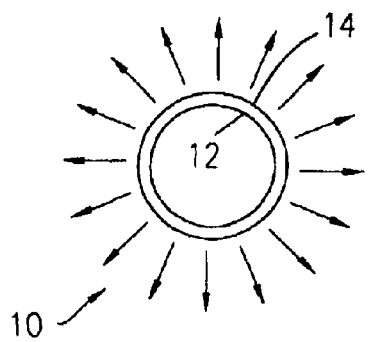
FIG. 1B is a schematic top plan view of the cylindrical piezoelectric transducer of FIG. 1A showing the direction of ultrasound energy emission therefrom.
Figure 1C:
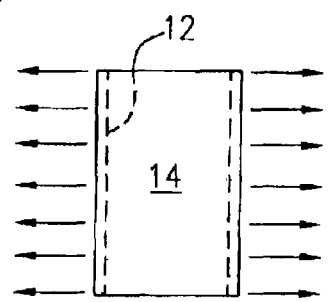
FIG. 1C is a schematic side elevational view of the cylindrical piezoelectric transducer of FIG. 1A showing the direction of ultrasound energy emission therefrom.

With reference initially to FIGS. 1A–1C a cylindrical piezoelectric transducer 10 is shown schematically from an elevational perspective view (FIG. 1A), from a top plan view (FIG. 1B) and from a front elevational view (FIG. 1C). More particularly, the cylindrical transducer 10 has an inner surface 12 and an outer surface 14. Both the inner and outer surfaces 12, 14 are coated with a conductive coating, such as gold, nickel, gold/chromium, etc., to provide electrical contact with the entire area of each surface 12, 14, while also avoiding electrical contact therebetween. The conductive coatings may be formed by vapor deposition, or any other suitable method that is known and understood to persons having ordinary skill in the art. An electrically conductive wire 16 is connected at one end thereof to the inner surface 12 and another electrically conductive wire 18 is connected at one end thereof to the outer surface 14 of the cylindrical transducer 10. Both wires 16, 18 are preferably a coaxial cable (not shown) and connected at their opposite ends to a source of electrical voltage, more particularly, an RF power source 20 (shown schematically only in FIG. 1A) so that a radiofrequency (RF) electrical voltage can be applied to the cylindrical transducer 10. The RF power source 20 typically operates at about 1–12 MHz. In operation, as shown schematically by the arrows in FIGS. 1B and 1C, when an RF voltage is applied to the cylindrical transducer 10, a collimated acoustical wave of ultrasound energy is emitted radially outwardly from the entire outer surface 14 of the cylindrical transducer 10, in a direction perpendicular to the outer surface 14.

Figure 2A:
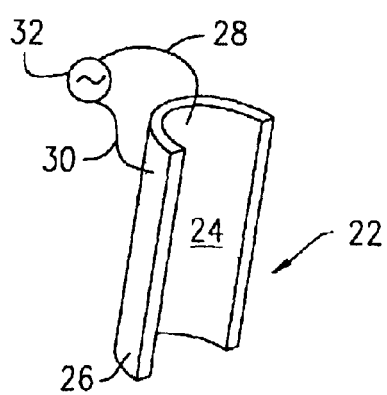
FIG. 2A is a schematic perspective view of a hemi-cylindrical piezoelectric transducer used in connection with certain embodiments of the present invention.
Figure 2B:
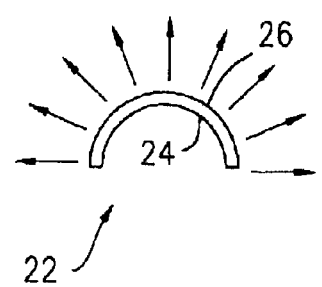
FIG. 2B is a schematic top plan view of the hemi-cylindrical piezoelectric transducer of FIG. 2A showing the direction of ultrasound energy emission therefrom.
Figure 2C:
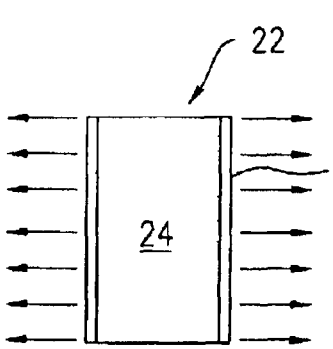
FIG. 2C is a schematic side elevational view of the hemi-cylindrical piezoelectric transducer of FIG. 2A showing the direction of ultrasound energy emission therefrom.

With reference now to FIGS. 2A–2C, a hemi-cylindrical piezoelectric transducer 22 is shown schematically from an elevational perspective view (FIG. 2A), from a top plan view (FIG. 2B) and from a front elevational view (FIG. 2C). More particularly, the hemi-cylindrical piezoelectric transducer 22 has an inner surface 24 and an outer surface 26, both of which are coated with a conductive coating, such as gold, nickel, gold/chromium, etc., to provide electrical contact with the entire area of each surface 24, 26, while also avoiding electrical contact therebetween. In a manner similar to that described hereinabove in connection with the cylindrical transducer 10, electrically conductive wires 28, 30, which are preferably a coaxial cable (not shown), are connected to the inner surface 24 and the outer surface 26, respectively, of the hemi-cylindrical transducer 22 and also to a source of electrical voltage, more particularly, an RF power source 32 (shown schematically only in FIG. 2A) so that a radiofrequency (RF) electrical current can be applied to the hemi-cylindrical transducer 10. The RF power source 32 typically operates at about 1–12 MHz. In operation, as shown schematically by the arrows in FIGS. 2B and 2C, when an RF voltage is applied to the hemi-cylindrical transducer 22, a collimated acoustical wave of ultrasound energy is emitted radially outwardly from the entire outer surface 26 of the hemi-cylindrical transducer 22, in a direction perpendicular to the outer surface 26.

When ultrasound energy is absorbed by tissue, it is converted into heat and, therefore, the tissue becomes heated. The RF power is supplied by the RF power sources 20, 32 at the resonant frequency of the transducers 10, 22, respectively, which is proportional to the thickness of each transducer 10, 22 between the inner and outer surfaces 12, 24, 14, 26, respectively, thereof. Typically, for use in connection with the present invention, the transducers 10, 22 should each be constructed having resonant frequencies ranging between about 4 to 12 MHz, preferably about 7 MHz. It is noted that the direction of ultrasound energy emissions from the transducers 10, 22 are easier to control than the direction of RF energy emissions from bipolar or monopolar RF devices known in the prior art. This is partly because the ultrasound energy emissions are collimated and partly because their direction of travel does not depend upon the placement of an antipolar electrode or ground plate, nor on tissue electrical properties that vary with tissue dessication that occurs during ablation. Since the transducers 10, 22 are directional, moving the transducer 10, 22 along a certain angle will also angle the ultrasonic acoustic field and redirect the tissue heating.

Since all three embodiments of the device of the present invention include one or more piezoelectric transducers of the two general types described hereinabove, and because the transducers are constructed and operated as described hereinabove, the transducers and their components shown in FIGS. 3–23 are labeled using variations of the reference numbers used in FIGS. 1A–1C and 2A–2C. For example, where the embodiment being discussed includes one or more cylindrical piezoelectric transducers like that described hereinabove, they will be labeled using reference number "10" followed by a lower-case letter, for example, 10a, 10b, 10c, etc. Where the embodiment being discussed includes one or more hemi-cylindrical piezoelectric transducers like that described hereinabove, they will be labeled using reference number "22" followed by a lower-case letter, for example 22a, 22b, 22c, etc. In addition, where the terms "distal" and "proximal" are used hereinafter in connection with the device of the present invention or components thereof, these terms refer to positions that are relative to the user, or surgeon, operating the device.

Figure 7:
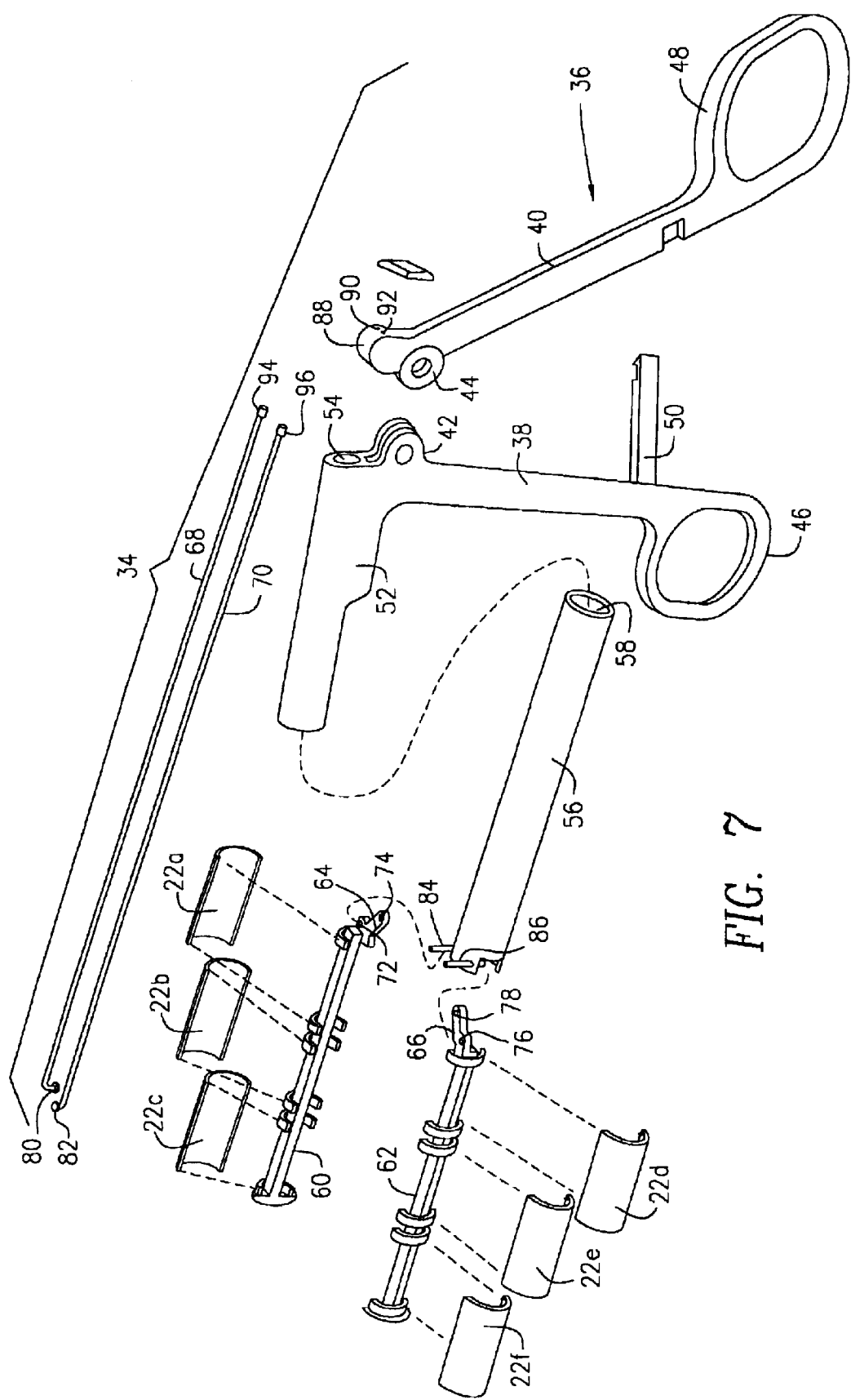
FIG. 7 is an exploded perspective view of the major components of the first embodiment of the device of FIG. 3.

With reference now to FIGS. 3–9, a first embodiment of a device 34 in accordance with the present invention is shown. More particularly, FIGS. 3 and 4 show the device 34 in an undeployed state in a perspective view and a top plan view, respectively. FIG. 5 shows a perspective view of the device 34 in a deployed state. The device 34 includes a handle 36 having a fixed arm 38 and a pivotable arm 40. The pivotable arm 40 is pivotably attached to the fixed arm 38 such that the handle provides means for manual manipulation and operation of the device 34, as will be described in further detail hereinafter. As seen in FIG. 7, the fixed and pivotable arms 38, 40 each include connecting means, such as connecting ears 42, 44 proximate to their distal ends, that cooperate in a manner known in the art to facilitate connecting the pivotable arm 40 to the fixed arm 38 in a pivotable manner. The fixed and pivotable arms 38, 40 of the first embodiment also each include a finger grip 46, 48 sized and shaped to receive the fingers of the surgeon therethrough for facilitating manual manipulation and operation of the device 34. The fixed arm 38 also includes a stop post 50 to prevent the pivotable arm 40 from moving too closely toward the fixed arm 38, thereby controlling the degree of deployment of the device 34, as explained in further detail hereinafter.

With further reference to FIGS. 3, 4, 5 and 7, the handle 36 also has a hollow shaft 52 that extends from the distal end of the fixed arm 38. The hollow shaft 52 has a through passage 54 and may be formed integrally with the fixed arm 38 or it may be formed as a separate component and attached to the fixed arm 38 by conventional means, such as welding or gluing. A hollow sleeve 56 also having a through passage 58 is connected to, and extends from, the distal end of the hollow shaft 52. The hollow sleeve 56 is sized and shaped to conform to the size and shape of the hollow shaft 52 such that their outer diameters are approximately equal and their through passages 54, 58, respectively, align with one another.

The device 34 also includes six hemi-cylindrical transducers 22a, 22b, 22c, 22d, 22e, 22f that are aligned and grouped with one another at the distal end of the hollow sleeve 56 as shown in FIGS. 3–9. More particularly, as can be seen in FIGS. 5 and 7, three of the hemi-cylindrical transducers 22a, 22b, 22c are securely mounted on a first carrier bar 60 such that their outer surfaces 24a, 24b, 24c all face one direction, which is perpendicular to the length of the first carrier bar 60. The other three hemi-cylindrical transducers 22d, 22e, 22f are securely mounted on a second carrier bar 62, such that their outer surfaces 24d, 24e, 24f all face a direction perpendicular to the length of the second carrier bar 62 and opposite that of the three hemi-cylindrical transducers 22a, 22b, 22c mounted on the first carrier bar 60. It is noted that, when the device 34 is in its undeployed state (see FIGS. 3 and 4), the six hemi-cylindrical transducers 22a, 22b, 22c, 22d, 22e, 22f are aligned and grouped with one another to form three pairs 22a–22d, 22b–22e, 22c–22f of transducers.

It is noted that, although not specifically shown in the figures, each of the hemi-cylindrical transducers 22a, 22b, 22c, 22d, 22e, 22f has a pair of electrically conductive wires (not shown) that are connected to their inner and outer surfaces, as well as to one or more RF power sources (not shown), as described hereinabove in connection with the construction and operation of the hemi-cylindrical transducer 22. To protect the wires, which are preferably coaxial cables (not shown), and minimize interference with the manipulation and operation of the device 34 by the surgeon, the aforesaid wires (not shown) can be attached to the hemi-cylindrical transducers 22a, 22b, 22c, 22d, 22e, 22f, and extended through the through passages 54, 58 of the hollow shaft 52 and hollow sleeve 56, to the RF power source or sources. As such, each hemi-cylindrical transducer 22a, 22b, 22c, 22d, 22e, 22f may have a separate power control if a multi-channel RF power source is used (not shown, but known to those of ordinary skill in the art). In this way, the thermal field and heating of tissue can be varied and further controlled.

In the foregoing arrangement, during operation of the device 34, ultrasound energy is emitted by the hemi-cylindrical transducers 22a, 22b, 22c, 22d, 22e, 22f in a radially outward direction, thereby approximating the directional effect of three cylindrical transducers when the device 34 is in an undeployed state (as shown in FIGS. 3 and 4). Furthermore, when the device 34 is in its deployed state, the carrier bars 60, 62 and also, therefore, the hemi-cylindrical transducers 22a, 22b, 22c, 22d, 22e, 22f mounted thereon, form a "V" shape (see FIGS. 5 and 6). When the device 34 is in its deployed state, the ultrasound energy is emitted by the hemi-cylindrical transducers 22a, 22b, 22c, 22d, 22e, 22f in the direction shown by the arrows in FIG. 6 (which shows the device 34 in use, in its deployed state, after insertion into the vagina 100 and uterus 98 of a female patient). The method of operating the device 34 in accordance with the present invention, as well as the advantages achieved thereby, will be described in further detail hereinafter.

With reference to FIGS. 5, 6 and 7, in particular, the proximal ends of the first and second carrier bars 60, 62 each have an extended tongue 64, 66, respectively, by which each of the first and second carrier bars 60, 62 is pivotably attached to the distal end of a corresponding actuator rod 68, 70, respectively. More specifically, as seen most clearly in FIGS. 7, 8 and 9, the extended tongue 64 of the first carrier bar 60 includes a first pivot hole 72 that is proximate to the first carrier bar 60 and a second pivot hole 74 that is remote from the first carrier bar 60 (in other words, proximate to the end of the extended tongue 64). The extended tongue 66 of the second carrier bar 62 includes a first pivot hole 76 that is proximate to the second carrier bar 62 and second pivot hole 78 that is remote from the second carrier bar 62 (in other words, proximate to the end of the extended tongue 66).

In addition, each of the actuator rods 68, 70 has a ninety-degree bend proximate its distal end, which forms a pivot hook 80, 82 on each actuator rod 68, 70, respectively. The pivot hooks 80, 82 of the actuator rods 68, 70 are each sized and shaped to fit into the first pivot hole 72, 76 of a corresponding one of the first and second carrier bars 60, 62, respectively (see FIGS. 7, 8 and 9). The hollow sleeve 56 has two pivot pins 84, 86 at its distal end that are each sized and shaped to be received through the second pivot hole 74, 78 of a corresponding one of the first and second carrier bars 60, 62, respectively (see FIGS. 7, 8 and 9).

Figure 8:
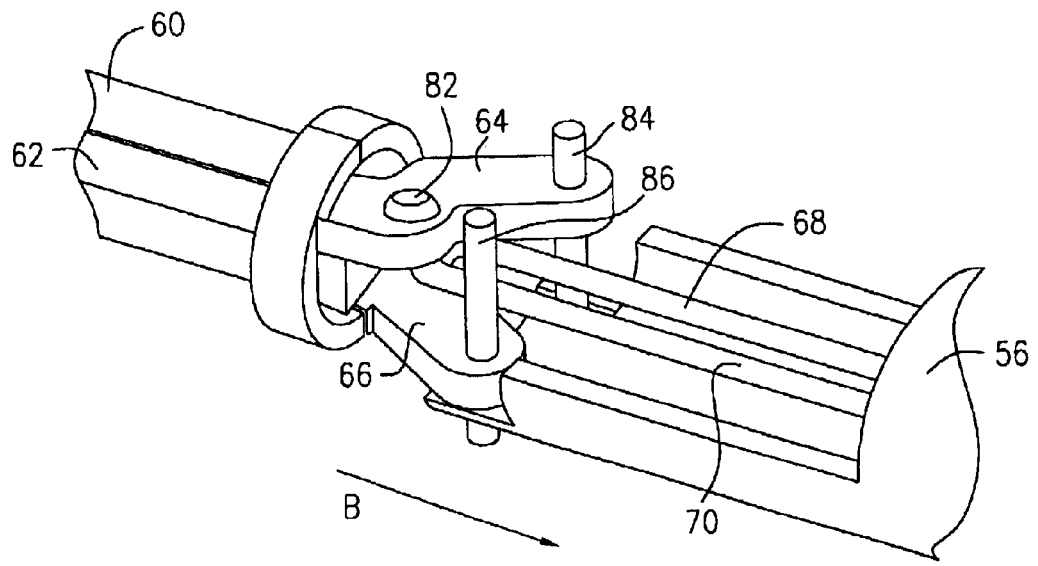
FIG. 8 is an enlarged perspective cut-away view of the connections between the carrier bars bearing the piezoelectric transducers and the actuator rods of the first embodiment of FIG. 3, with the device in the undeployed state.
Figure 9:
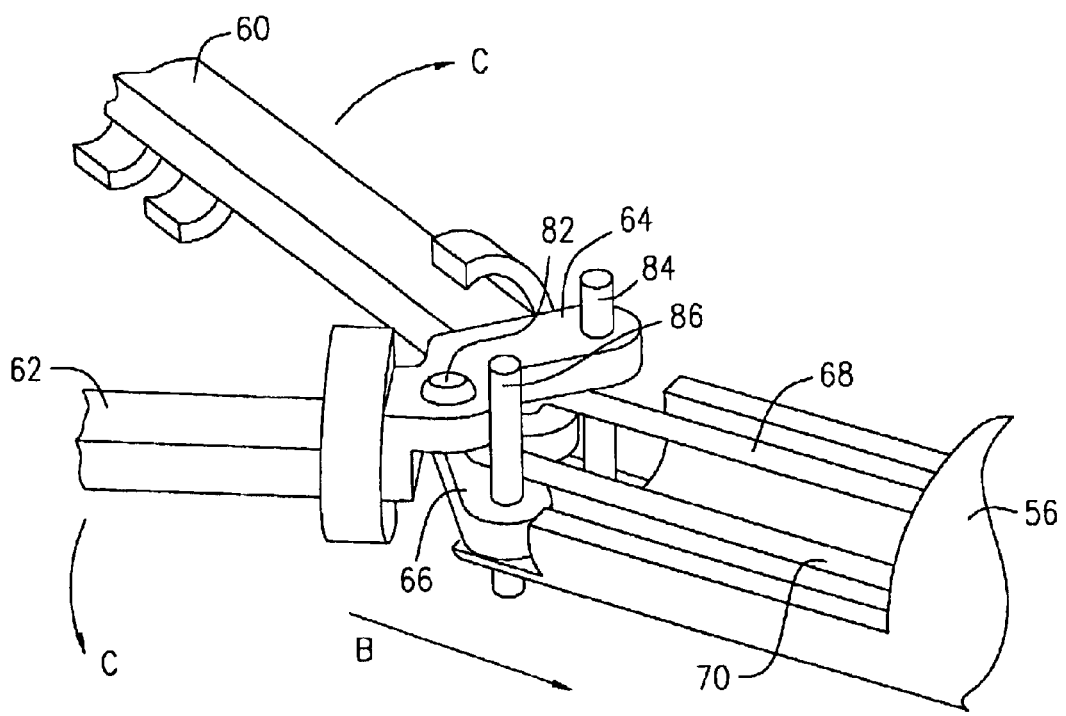
FIG. 9 is an enlarged perspective cut-away view of the connections between the carrier bars bearing the piezoelectric transducers and the actuator rods of the first embodiment of FIG. 5, with the device in the deployed state.

With continued reference to FIGS. 7, 8 and 9, it is noted that the positions of each of the pivot pins 84, 86 of the hollow sleeve 56 are stationary relative to the hollow sleeve 56 and relative to the first and second carrier bars 60, 62. Thus, when the pivot pins 84, 86 of the hollow sleeve 56 are received within the second pivot holes 74, 78 of the first and second carrier bars 60, 62, respectively, they form the pivot point of each of the first and second carrier bars 60, 62 thereby allowing the first and second carrier bars 60, 62, with the hemi-cylindrical transducers 22a, 22b, 22c, 22d, 22e, 22f mounted thereon, to form the abovementioned "V" shape. As seen most clearly in FIGS. 8 and 9, when the pivot hooks 80, 82 of the actuator rods 68, 70 are received within the first pivot holes 72, 76 of the first and second carrier bars 60, 62, respectively, the distal ends of the actuator rods 68, 70 extend together in between the pivot pins 84, 86 of the hollow sleeve 56. The purpose of the foregoing arrangement of pivot holes 72, 74, 76, 78, pivot hooks 80, 82 and pivot pins 84, 86 will become apparent hereinafter during discussion of the operation of the device 34.

With reference now specifically to FIGS. 3, 4 and 7, the actuator rods 68, 70 are slidingly received in the through passages 58, 54 of the hollow sleeve 56 and the hollow shaft 52, respectively, and extend together from the first and second carrier bars 60, 62, through the through passages 58, 54, and out of the proximal end of the hollow shaft 52. The proximal end of each actuator rod 68, 70 is affixed to the distal end 88 of the pivotable arm 40. More particularly, the proximal end of each actuator rod 68, 70 is inserted through one of a pair of holes 90, 92 provided in the distal end 88 of the pivotable arm 40 (see FIG. 7) and the proximal end of each actuator rod 68, 70 includes an enlarged stop 94, 96, respectively, thereon for retaining the proximal ends of the actuator rods 68, 70 through the holes 90, 92.

With reference to the overall size and shape of the device 34, it is noted that while the device 34 of the present invention may be adapted for ablation of tissue within cavities or lumens other than the uterus, the embodiments disclosed herein are intended for use in performing endometrial ablation and, therefore, they are sized and shaped to be inserted and operated within the uterus of a patient. More particularly, the sum of the lengths of the hollow shaft 52 and hollow sleeve 56 should be between about 15 and 50 centimeters (cm), preferably about 25 cm. Regarding the individual lengths of these components, the length of the hollow shaft 52 should be from about 5 to 15 cm, preferably about 10 cm, and the length of the hollow sleeve 56 should be from about 10 to 35 cm, preferably 15 cm. Moreover, the outer diameters of the hollow shaft 52 and the hollow sleeve 56 should be substantially the same as one another and, more specifically, from approximately 5 to 10 millimeters (mm), preferably about 5 mm. The diameter of the through passages 54, 58 of the hollow shaft 52 and the hollow sleeve 56, respectively, should be large enough to slidingly receive therethrough both actuator rods 68, 70 and all of the wires (not shown) attached to the hemi-cylindrical transducers 22a, 22b, 22c, 22d, 22e, 22f, more particularly, from about 3 mm to 8 mm, preferably about 3.5 mm. In addition, the lengths of the first and second carrier bars 60, 62 should be the same as one another and be between about 3 and 6 cm, preferably about 4 cm.

With regard to the size of the hemi-cylindrical transducers 22a, 22b, 22c, 22d, 22e, 22f, it is noted that although they are shown in FIGS. 3–9 as being of the same size as one another, they do not have to be the same size and, in fact, may be differently sized. It is preferable, however, that the members of each pair of hemi-cylindrical transducers (for example, 22a–22d, 22b–22e, 22c–22f in FIG. 3) should be the same size as each other. In the present embodiment of the device 34, each hemi-cylindrical transducer 22a, 22b, 22c, 22d, 22e, 22f is between about 1 and 3 cm long, preferably about 1.5 cm long. In addition, each hemi-cylindrical transducer 22a, 22b, 22c, 22d, 22e, 22f is about 5 to 10 millimeters (mm) wide at its greater width, such that the pairs of hemi-cylindrical transducers 22a–22d, 22b–22e, 22c–22f approximate the shape of three cylindrical transducers having an overall diameter of about 5 to 10 mm, preferably about 5 mm.

The method of using the device 34 to perform endometrial ablation will now be described. Initially, it is noted that the device 34 of the present invention may be used in conjunction with a fluid-filled balloon, such as is well-known in the art for treating the endometrium, or it may be used without such a balloon and, instead the uterus should be filled with fluid. The fluid is required to provide a means for the ultrasound energy emitted from the ultrasound transducers to travel to, and be absorbed by, the endometrial tissues to be treated. For purposes of the following discussion, the uterus will be prepared for surgery and filled with a suitable fluid, such as saline, in a manner that is well-known to those of ordinary skill in the art and consistent with currently accepted medical/surgical standards.

With reference now to FIG. 6, after the uterus has been prepared and filled with fluid, as described above, the device 34 in its undeployed state (see FIGS. 3 and 4) is inserted into the uterus 98 of a patient. More particularly, the device 34 is held by the finger grips 46, 48 of the handle 36 by the surgeon and the first and second carrier bars 60, 62 (with the undeployed hemi-cylindrical transducers 22a, 22b, 22c, 22d, 22e, 22f mounted thereon) and at least a portion of the hollow sleeve 56 are inserted through the vagina 100 and into the uterus 98. The hemi-cylindrical transducers 22a, 22b, 22c, 22d, 22e, 22f are positioned approximately centrally within the uterus 98, or at an otherwise appropriate position within the uterus as clinically determined by the surgeon. With reference now to FIG. 5, the device 34 is then deployed by squeezing the fixed and pivotable arms 38, 40 together such that the pivotable arm 40 moves toward the fixed arm 38 as far as the stop post 50, which causes the distal end 88 of the pivotable arm 40 to move away from the fixed arm 38 and the hollow shaft 52 in the direction indicated by the arrow A in FIG. 5. When the distal end 88 of the pivotable arm 40 moves away from the fixed arm 38, the actuator rods 68, 70 are pulled through the through passages 54, 58 and the pivot hooks 80, 82 at the distal ends of the actuator rods 68, 70 are moved toward the hollow sleeve 56 in the direction indicated by the arrow B in FIGS. 5, 8 and 9, which, in turn, causes the first and second carrier bars 60, 62 to move away from one another, as indicated by the arrows C in FIGS. 5 and 9, into a deployed "V" shape. The RF power source (not shown) is then turned on, which causes RF power to be delivered to the hemi-cylindrical transducers 22a, 22b, 22c, 22d, 22e, 22f which causes them to emit ultrasound energy, as shown by the arrows in FIG. 6, which travels to the endometrial tissue where it is absorbed, resulting in heating and ablation of the tissue. After a period of time, which is clinically determined by the surgeon, the RF power source (not shown) is turned off, which ceases the ultrasound energy emissions from the hemi-cylindrical transducers 22a, 22b, 22c, 22d, 22e, 22f. Typically, the period of time between turning the RF power source on and turning it off is between about 2 and 10 minutes, but no more than about 20 minutes and preferably from about 2 to 3 minutes.

As shown in FIG. 6, the lateral walls 102, 104 of the uterus 98 and also, therefore, a portion of the endometrium 106, are sloped. When the device 34 is in its deployed state, the outer surfaces 24a, 24b, 24c, 24d, 24e, 24f of the hemi-cylindrical transducers 22a, 22b, 22c, 22d, 22e, 22f are substantially aligned with the sloping portion of the endometrium 106 such that the ultrasound energy emitted by the hemi-cylindrical transducers 22a, 22b, 22c, 22d, 22e, 22f will contact the sloping portion of the endometrium 106 from a direction that is nearly perpendicular thereto, which maximizes the amount of heat energy that will be received by the endometrial tissue at this location. During in situ operation of the device 34, the device 34 can be moved, for example back and forth or tilted, such that the carrier bars 60, 62 and the hemi-cylindrical transducers 22a, 22b, 22c, 22d, 22e, 22f mounted thereon are also so moved within the uterus 98 of the patient. Such movement will direct at least a portion of the ultrasound energy from the hemi-cylindrical transducers 22a, 22b, 22c, 22d, 22e, 22f upward to heat and ablate the upper endometrial tissue.

Figures 10, 11:
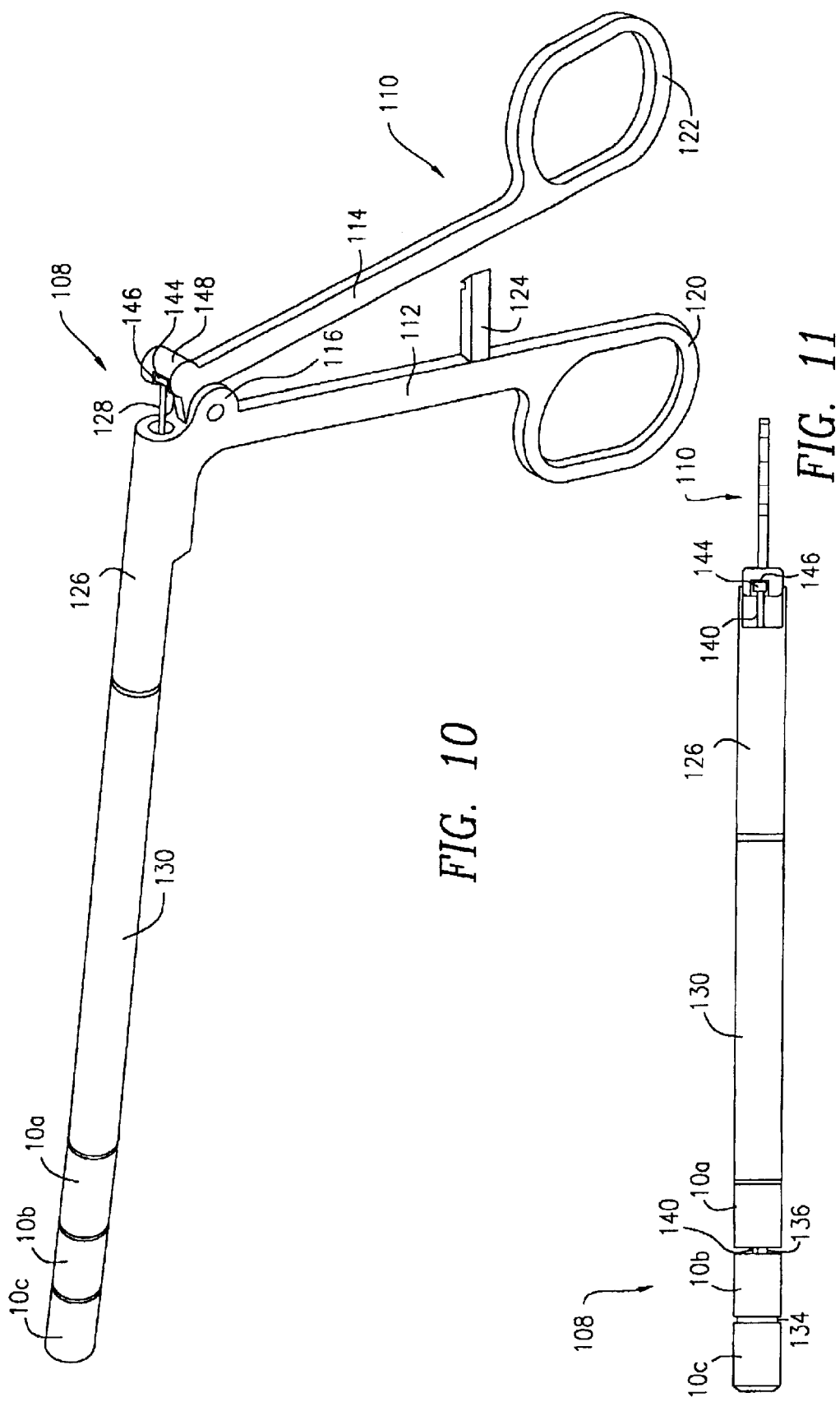
FIG. 10 is a perspective view of a second embodiment of the device of the present invention, in an undeployed state.
FIG. 11 is a top plan view of the second embodiment of the device of FIG. 10.
Figure 12:
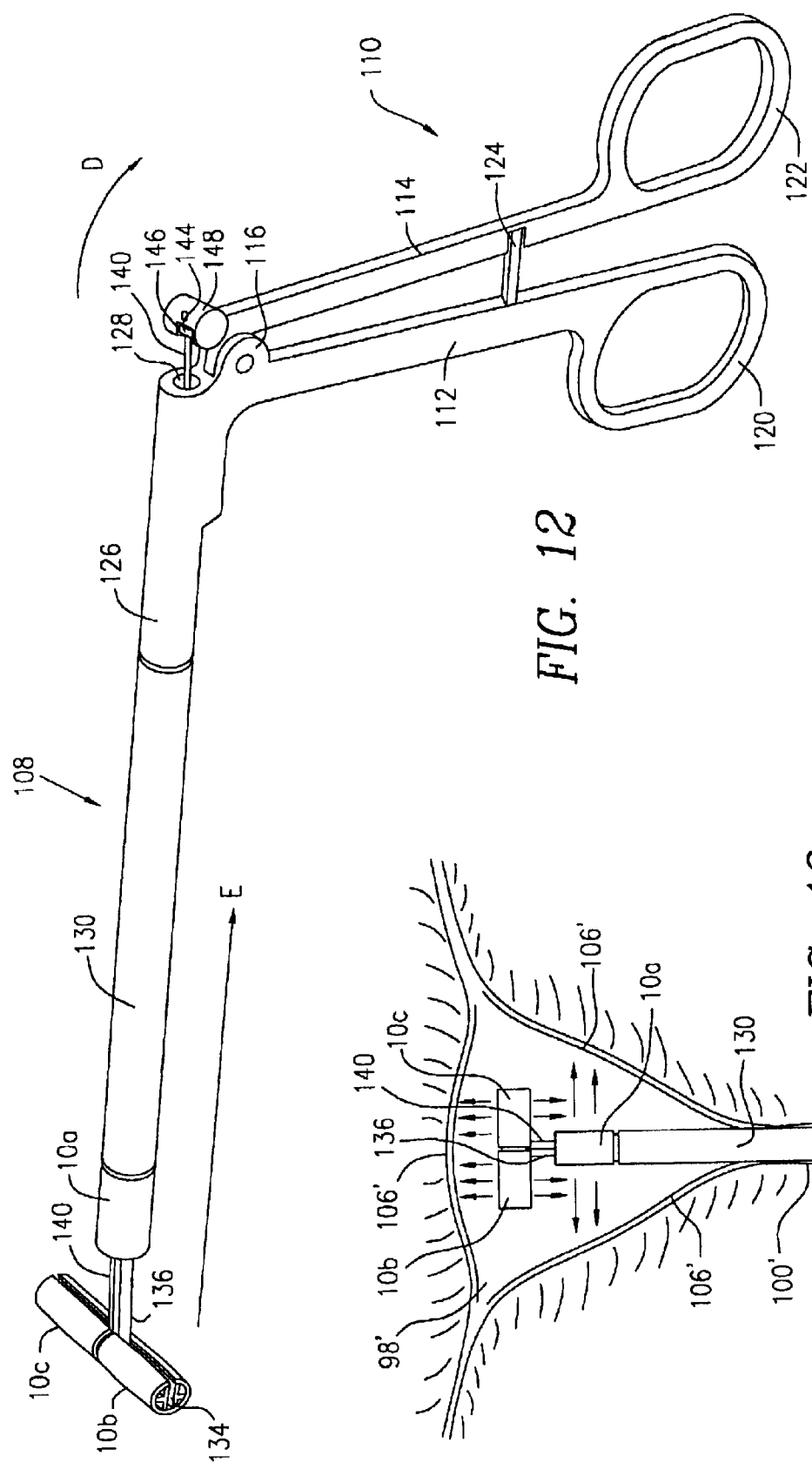
FIG. 12 is a perspective view of the second embodiment of the device of FIG. 10, in a deployed state.
Figure 13:
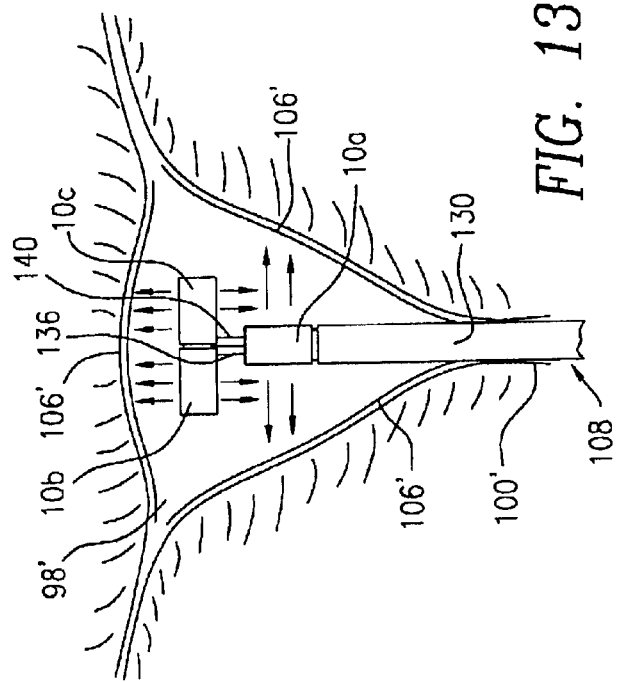
FIG. 13 is a schematic cut away view of the second embodiment of the device of FIG. 12, in a deployed state, positioned within the uterus of a patient and showing, schematically, the direction of emission of ultrasound energy from the transducers.
Figure 14:
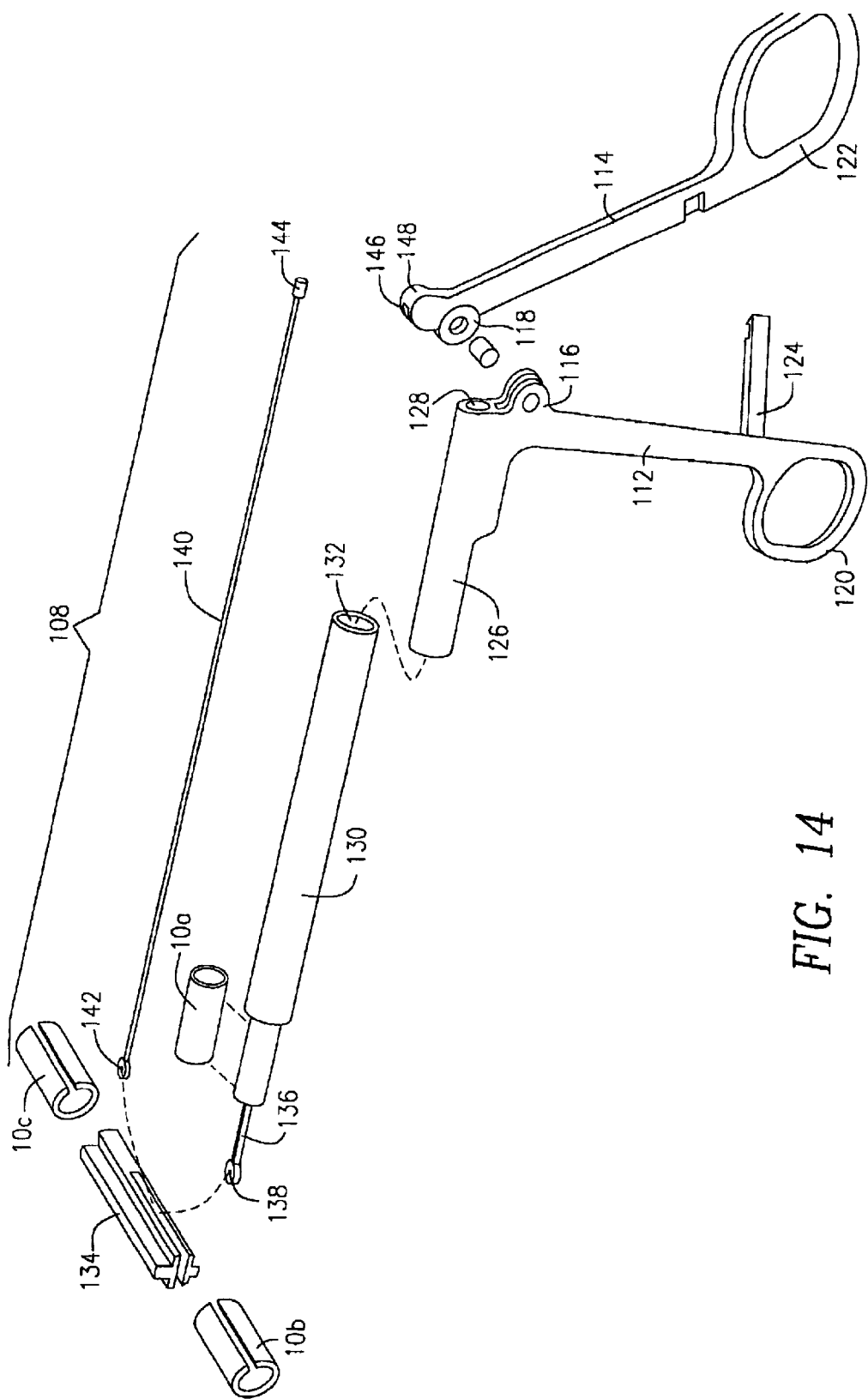
FIG. 14 is an exploded perspective view of the major components of the second embodiment of the device of FIG. 10.
Figure 15:
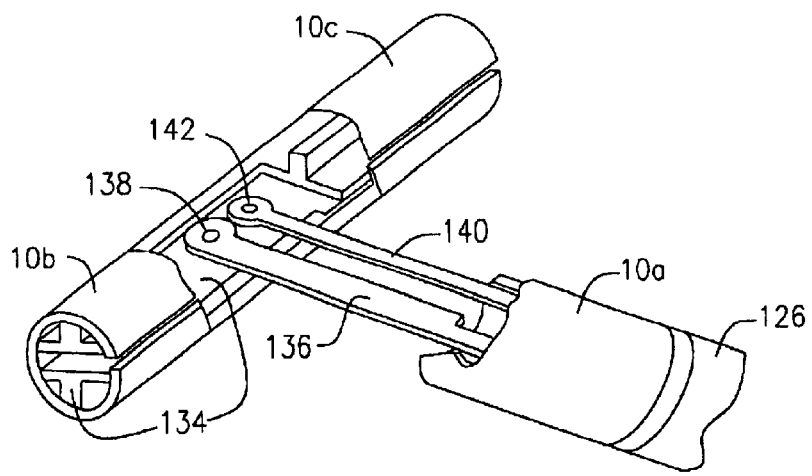
FIG. 15 is an enlarged perspective cut-away view of the connections between the carrier bar bearing the piezoelectric transducer and the actuator rods of the second embodiment of FIG. 12, with the device in the deployed state.

With reference now to FIGS. 10–16C, a second embodiment of the device 108 in accordance with the present invention is shown. More particularly, FIGS. 10 and 11 show the device 108 in an undeployed state in a perspective view and a top plan view, respectively. FIG. 12 shows a perspective view of the device 108 in a deployed state. The device 108 includes a handle 110 having a fixed arm 112 and a pivotable arm 114. The pivotable arm 114 is pivotably attached to the fixed arm 112 such that the handle 110 provides means for manual manipulation and operation of the device 108, as will be described in further detail hereinafter. As seen in FIG. 14, the fixed and pivotable arms 112, 114 each include connecting means, such as connecting ears 116, 118 proximate to their distal ends, that cooperate in a manner known in the art to facilitate connecting the pivotable arm 114 to the fixed arm 112 in a pivotable manner. The fixed and pivotable arms 112, 114 of the first embodiment also each include a finger grip 120, 122 sized and shaped to receive the fingers of the surgeon therethrough for facilitating manual manipulation and operation of the device 108. The fixed arm 112 also includes a stop post 124 to prevent the pivotable arm 114 from moving too closely toward the fixed arm 112, thereby controlling the degree of deployment of the device 108, as explained in further detail hereinafter.

With further reference to FIGS. 10, 11, 12 and 14, the handle 110 also has a hollow shaft 126 that extends from the distal end of the fixed arm 112. The hollow shaft 126 has a through passage 128 and may be formed integrally with the fixed arm 112 or it may be formed as a separate component and attached to the fixed arm 112 by conventional means, such as welding or gluing. A hollow sleeve 130 also having a through passage 132 is connected to, and extends from, the distal end of the hollow shaft 126. The hollow sleeve 130 is sized and shaped to conform to the size and shape of the hollow shaft 126 such that their outer diameters are approximately equal and their through passages 128, 132, respectively, align with one another.

The device 108 also includes a cylindrical transducer 10a positioned proximate to the distal end of the hollow sleeve 130, as well as two incomplete cylindrical transducers 10b, 10c mounted upon a carrier 134 that is positioned proximate to the cylindrical transducer 10a. Furthermore, the carrier 134 is pivotably attached, at a location intermediate its ends, to the distal end of a stationary bar 136 that has a hole 138 therethrough for such pivotable attachment (see FIGS. 14 and 15). The proximal end of the stationary bar 136 is attached to the distal end of the hollow sleeve 130 and the stationary bar 136 extends out of the hollow sleeve 130 and completely through the interior of the cylindrical transducer 10a (see FIGS. 15 and 16A–16C).

With reference to FIGS. 12, 13 and 14, in particular, the device 108 also includes an actuator rod 140 with a hole 142 at its distal end and an enlarged plug 144 at its proximate end. The actuator rod 140 is slidingly received within the through passages 132, 128 of the hollow sleeve 130 and the hollow shaft 126 and is pivotably attached at its distal end to the carrier 134, at a position that is proximate to the position at which the stationary bar 136 is attached to the carrier 134 (see FIGS. 15 and 16A–16C). Furthermore, the enlarged plug 144 of the actuator rod 140 is received within a recess 146 provided in the distal end 148 of the pivotable arm 114 of the handle 110.

It is noted that, although not specifically shown in the figures, the cylindrical transducer 10a and the incomplete cylindrical transducers 10b, 10c each have a pair of electrically conductive wires (not shown), preferably as a coaxial cable (not shown), that are connected to their inner and outer surfaces, as well as to one or more RF power sources (not shown), as described hereinabove in connection with the construction and operation of the cylindrical transducer 10. To protect the wires and minimize interference with the manipulation and operation of the device 108 by the surgeon, the aforesaid wires (not shown) can be attached to the cylindrical transducer 10a and the incomplete cylindrical transducers 10b, 10c and extended through the through passages 128, 132 of the hollow shaft 126 and hollow sleeve 130, to the RF power source (not shown).

In the foregoing arrangement, during operation of the device 108, when RF power is supplied to the transducers 10a, 10b, 10c, ultrasound energy is emitted by the cylindrical transducer 10a in a radially outward direction, as discussed hereinabove in connection with the typical cylindrical transducer 10. Furthermore, when the device 108 is in its deployed state, the carrier 134 and also, therefore, the incomplete cylindrical transducers 10b, 10c mounted thereon, are oriented perpendicularly to the cylindrical transducer 10a (see FIGS. 12 and 15) and ultrasound energy is emitted by the incomplete cylindrical transducers 10b, 10c in the direction shown by the arrows in FIG. 13 (which shows the device 108 in use, in its deployed state, after insertion into the vagina 100' and uterus 98' of a female patient). The method of operating the device 108 in accordance with the present invention, as well as the advantages achieved thereby, will be described in further detail hereinafter.

Figure 16C:
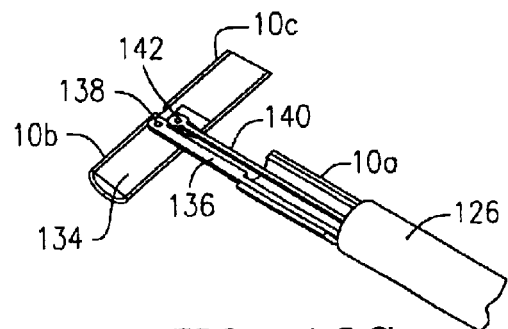
FIGS. 16A–16C are sequential perspective cut-away views of the piezoelectric transducer and the actuator rods of the second embodiment of FIG. 11, showing the progressive movement of the transducer and actuator rods from the undeployed state to the deployed state.
Figure 16B:
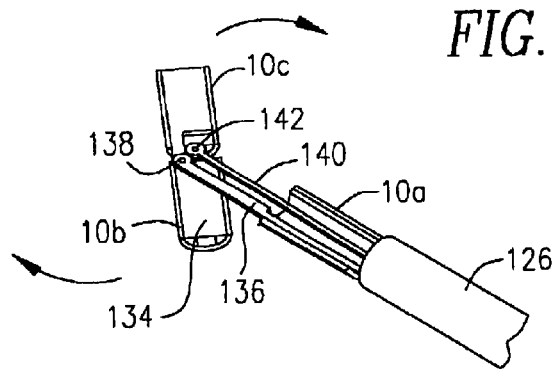
Figure 16A:
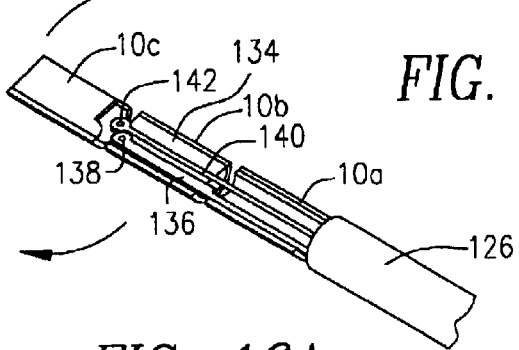

With reference now to FIGS. 15 and 16A–16C, it is noted that the position of the stationary bar 136 which extends from the hollow sleeve 130 is stationary relative to the hollow sleeve 130 and relative to the cylindrical transducer 10a. Thus, the connection between the carrier 134 and the distal end of the stationary bar 136 forms the pivot point of the carrier 134. As shown in FIGS. 16A–16C, the carrier 134, with the incomplete cylindrical transducers 10b, 10c mounted thereon, is pivotable between an undeployed position (shown in FIGS. 10, 11 and 16A), wherein the incomplete cylindrical transducers 10b, 10c align longitudinally with the cylindrical transducer 10a and the hollow sleeve 130, and a deployed position (shown in FIGS. 12 16C), wherein the incomplete cylindrical transducers 10b, 10c are aligned perpendicularly to the cylindrical transducer 10a and the hollow sleeve 130. More particularly, when the fixed and pivotable arms 112, 114 of the handle 110 are squeezed together, the pivotable arm 114 moves toward the fixed arm 112 as far as the stop post 124 which causes the distal end 148 of the pivotable arm 114 to move away from the fixed arm 112 and the hollow shaft 126, in the direction indicated by the arrow D in FIG. 12. When the distal end 148 of the pivotable arm 114 moves away from the fixed arm 112, the actuator rod 140 is pulled through the through passages 128, 132 in the direction indicated by the arrow E in FIG. 12 and, as shown in the sequential cut away views of FIGS. 16A–16C, the actuator rod 140 pulls the carrier 134 from its undeployed position (FIG. 16A) to its deployed position (FIG. 16C), which results in the repositioning of the incomplete cylindrical transducers 10b, 10c such that they are oriented perpendicularly to the cylindrical transducer 10a.

With reference to the overall size and shape of the device 108, the sum of the lengths of the hollow shaft 126 and hollow sleeve 130 should be between about 15 and 20 cm, preferably about 25 cm. Regarding the individual lengths of these components, the length of the hollow shaft 126 should be from about 5 to 15 cm, preferably about 10 cm, and the length of the hollow sleeve 130 should be from about 10 to 35 cm, preferably 15 cm. Moreover, the outer diameters of the hollow shaft 126 and the hollow sleeve 130 should be substantially the same as one another and, more specifically, from approximately 5 to 10 mm, preferably about 5 mm. The diameter of the through passages 128, 132 of the hollow shaft 126 and the hollow sleeve 130, respectively, should be large enough to slidingly receive therethrough the actuator rod 140 (without interfering with the stationary bar 136) and all of the wires (not shown) attached to the cylindrical transducer 10a and the incomplete cylindrical transducers 10b, 10c. More particularly, the diameter of the through passages 128, 132 should be from about 3 mm to 15 mm, preferably about 5 mm in diameter. In addition, the length of the carrier 134 should be between about 2 and 3 cm, preferably about 3 cm.

With regard to the size of the cylindrical transducer 10a and the incomplete cylindrical transducers 10b, 10c, it is noted that, although they are shown in FIGS. 3–9 as being of the same general size as one another, they do not have to be the same size and, in fact, may be differently sized. It is preferable, however, that the two transducers 10b, 10c that are mounted onto the carrier 134 be of similar size and shape to one another. In the present embodiment of the device 108, each of the transducers 10a, 10b, 10c is between about 1 and 3 cm long, preferably about 1.5 cm long and about 5 to 10 in diameter, preferably about 5 mm in diameter.

The method of operating the device 108 of the second embodiment to perform endometrial ablation will now be described. Initially, it is noted that, like the device 34 of the first embodiment discussed hereinabove, the device 108 of the second embodiment may be used in conjunction with a fluid-filled balloon, such as is well-known in the art for treating the endometrium, or it may be used without such a balloon and, instead the uterus should be filled with fluid.

With reference now to FIG. 13, after the uterus 98' has been prepared and filled with fluid, as described hereinabove, the device 108 in its undeployed state (see FIGS. 10 and 11) is inserted into the uterus 98' of a patient. More particularly, the device 108 is held by the finger grips 120, 122 of the handle 110 by the surgeon and the carrier 134 (with the cylindrical transducer 10a and undeployed incomplete cylindrical transducers 10b, 10c mounted thereon) and at least a portion of the hollow sleeve 130 are inserted through the vagina 100' and into the uterus 98'. The transducers 10a, 10b, 10c are positioned approximately centrally within the uterus 98', or at an otherwise appropriate position within the uterus as clinically determined by the surgeon. The device 108 is then deployed, as described above in connection with FIGS. 15 and 16A–16C, by squeezing the fixed and pivotable arms 112, 114 together such that the carrier 134 is moved to its deployed position and the incomplete transducers 10b, 10c are reoriented to be perpendicular to the cylindrical transducer 10a and hollow sleeve 130. The RF power source (not shown) is then turned on, which causes RF power to be delivered to the transducers 10a, 10b, 10c, which causes them to emit ultrasound energy, as shown by the arrows in FIG. 13, that travels to the endometrium 106' where it is absorbed, resulting in heating and ablation of the endometrial tissue. After a period of time, which is clinically determined by the surgeon, the RF power source (not shown) is turned off, which ceases the ultrasound energy emissions from the transducers 10a, 10b, 10c. Typically, the period of time between turning the RF power source on and turning it off is between about 2 and 10 minutes, but no more than about 20 minutes and preferably from about 2 to 3 minutes.

As can be seen from viewing FIG. 13, the ultrasound energy emitted by the transducers 10a, 10b, 10c when the device 108 is in its deployed state achieves wider coverage of the endometrium 106' than the ultrasound energy that would be emitted from a device having only longitudinally aligned transducers (such as, for example, the arrangement of the transducers 10a, 10b, 10c when the device 108 is in its undeployed state as in FIG. 10). More particularly, in its deployed state, the device 108 delivers ultrasound energy directly to the top wall 150' of the uterus 98', which would otherwise be nearly entirely neglected by existing devices having only longitudinally aligned transducers. As with the device 34 of the first embodiment, the device 108 of the second embodiment can be moved, for example back and forth or tilted, during in situ use such that the transducers 10a, 10b, 10c are also so moved within the uterus 98 of the patient. Such movement will allow the surgeon to have greater directional control of at least a portion of the ultrasound energy that is emitted from the transducers 10a, 10b, 10c toward the endometrial tissue.

Figure 19:
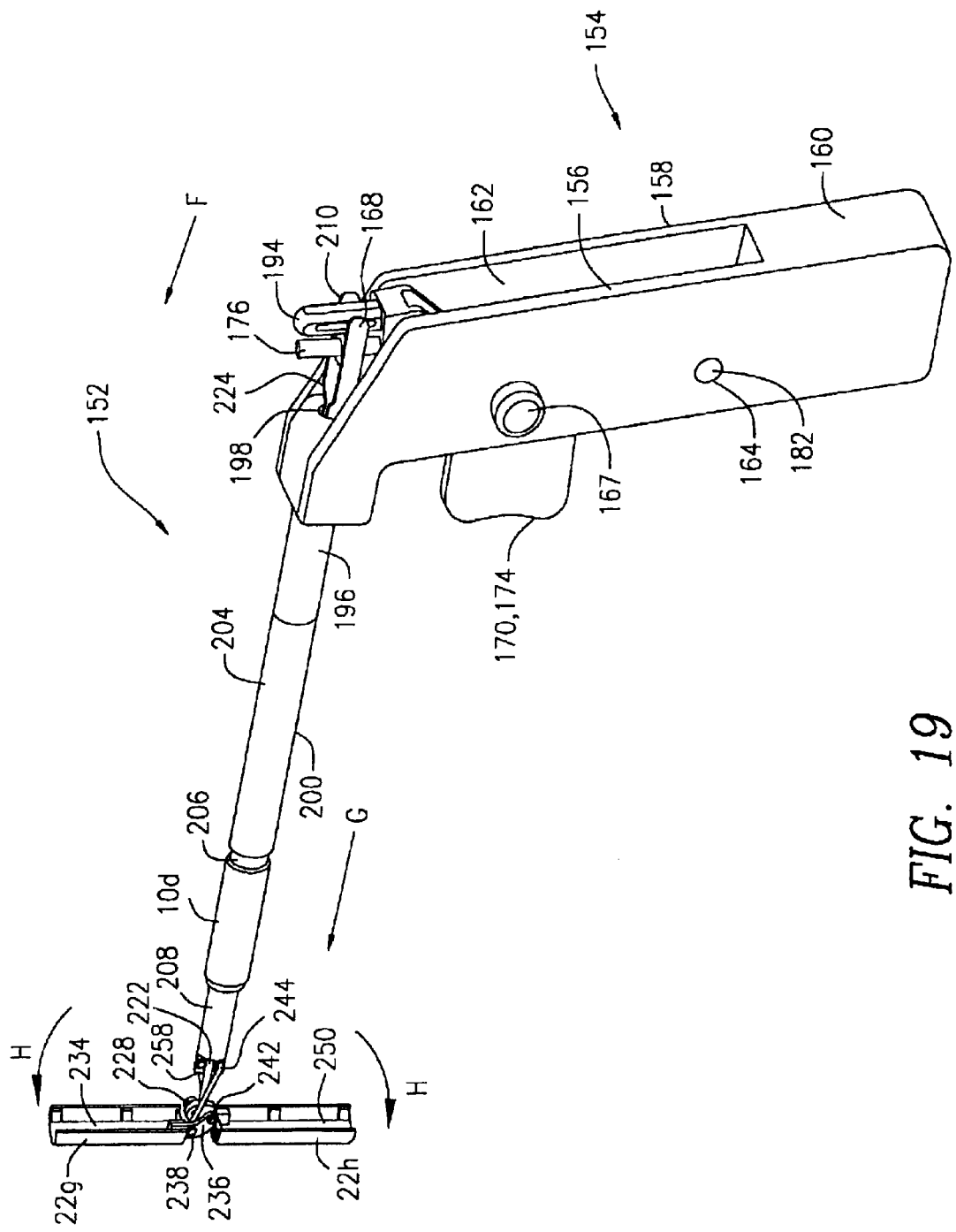
FIG. 19 is a perspective view of the third embodiment of the device of FIG. 17, in a deployed and extended state.

With reference now to FIGS. 17–23, a third embodiment of the device 152 in accordance with the present invention is shown. More particularly, FIGS. 17 and 18 show the device 152 in an undeployed and extended state in a perspective view and a top plan view, respectively. FIG. 19 shows a perspective view of the device 152 in a deployed and extended state, while FIG. 20 shows a perspective view of the device 152 in a fully deployed and retracted state.

With reference in particular to FIGS. 17–20 and 22, the device 152 includes a handle 154 with lateral walls 156, 158 and a bottom portion 160 that form a cavity 162 therebetween. The handle 154 includes a first pair of aligned holes 164 (only one of which is visible) through the lateral walls 156, 158 and a second pair of aligned holes 166 (only one of which is visible) through the lateral walls, for a purpose to be explained hereinafter. The handle 154 also includes a deploying lever 168 and a retraction trigger 170 that are sized and shaped to fit at least partly within the cavity 162, as described hereinafter.

Figure 22:
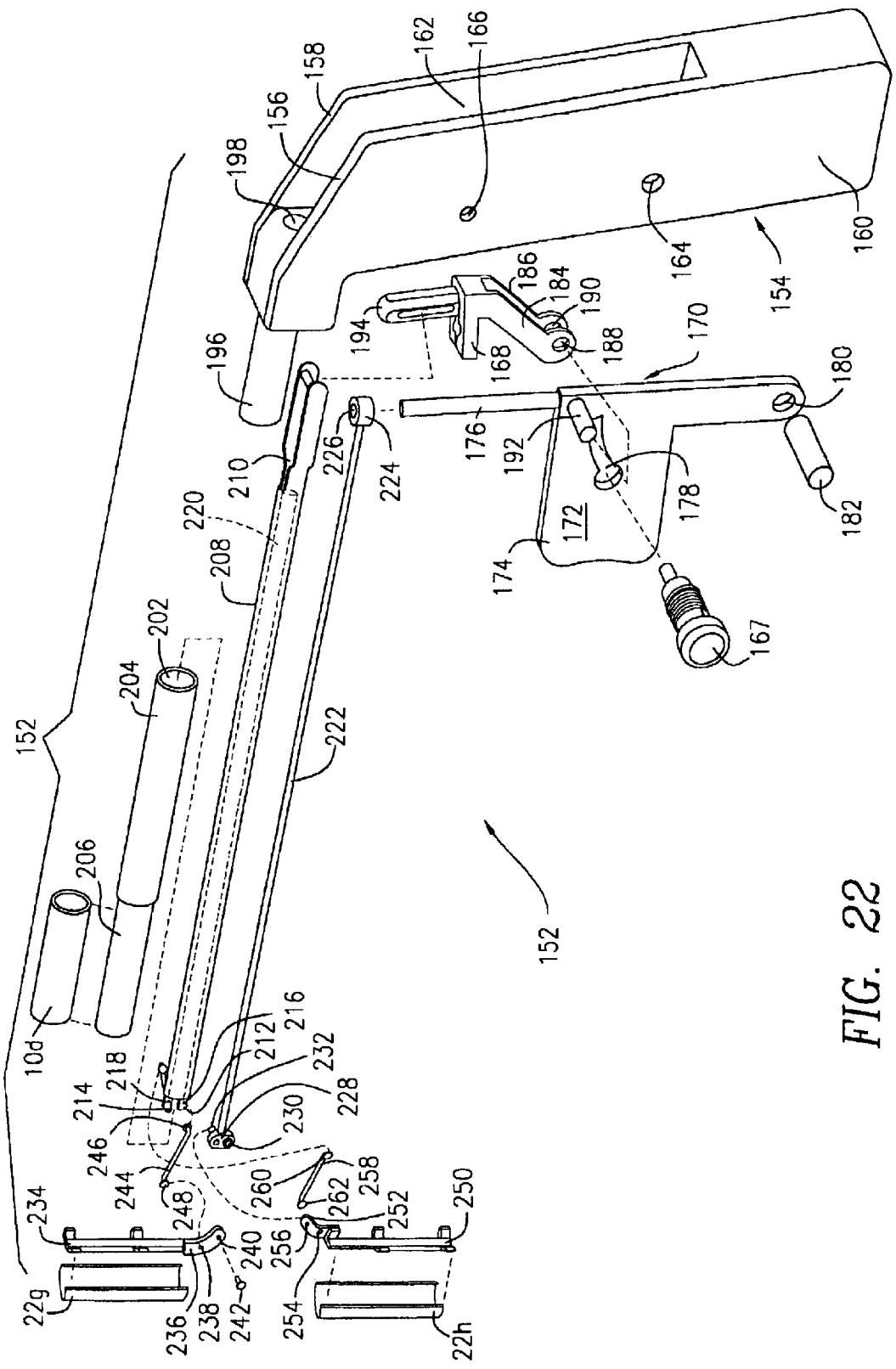
FIG. 22 is an exploded perspective view of the major components of the third embodiment of the device of FIG. 17.
Figure 23:
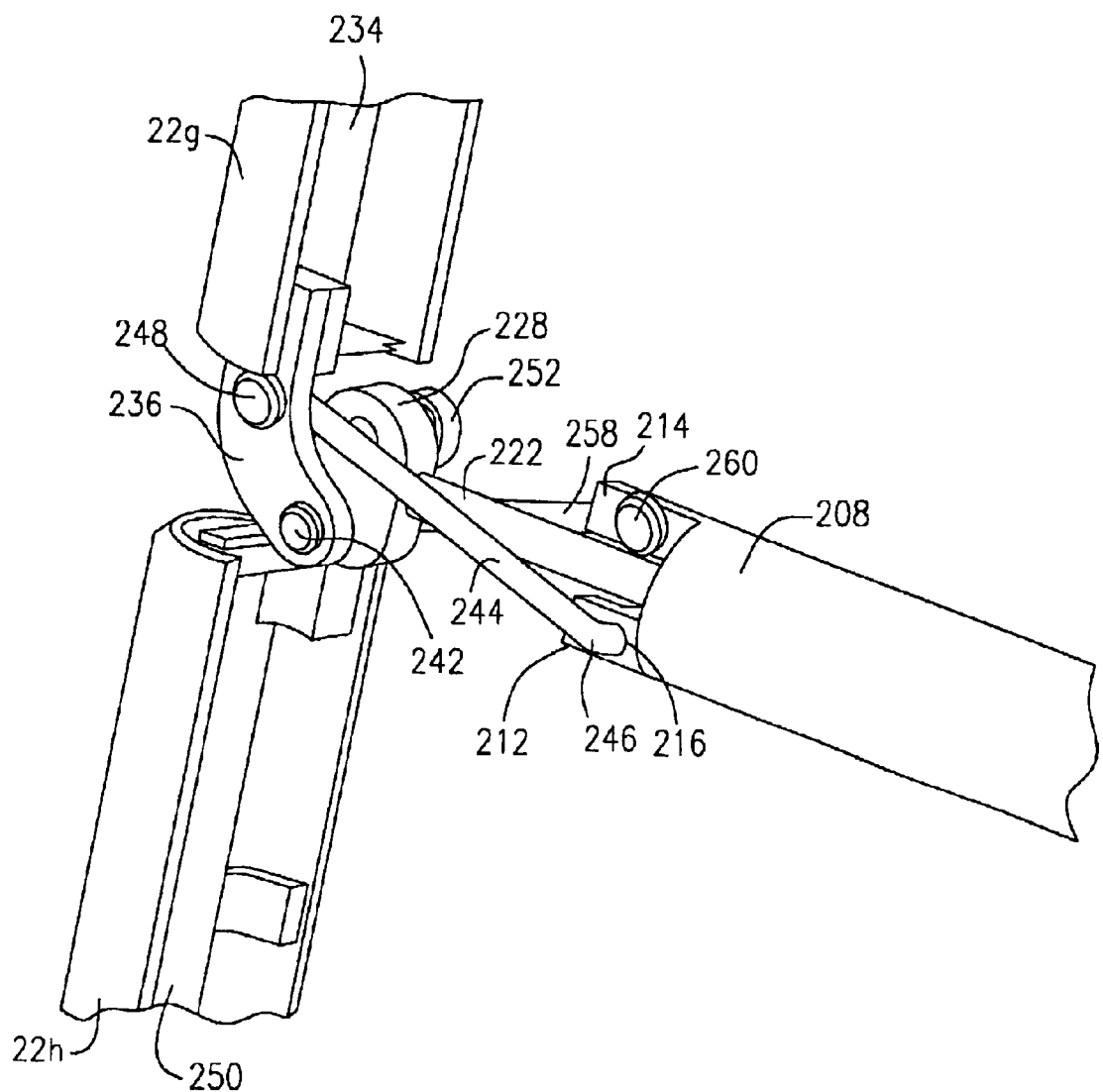
FIG. 23 is an enlarged perspective cut-away view of the connections between the carrier bars bearing the piezoelectric transducers and the actuator rods of the third embodiment of FIG. 17, with the device in the deployed state.

More particularly, with reference to FIG. 22, the retraction trigger 170 has a planar body 172 with a finger pad 174 and a post 176 extending therefrom and an elongate slot 178. When the retraction trigger 170 is positioned within the cavity 162 of the handle 154, a pivot hole 180 on the planar body 172 aligns with the first pair of holes 164 (only one of which is visible) and a pin 182 is inserted therethrough, thereby pivotably mounting the retraction trigger 170 within the cavity 162. In addition, the elongate slot 178 on the planar body 172 aligns with the second pair of aligned holes 166 (only one of which is visible) and a bolt 167 is inserted therethrough, whereby the retraction trigger 170 is pivotable between a predetermined extended position (shown in FIGS. 17 and 19) and a predetermined retracted position (see FIG. 20). Furthermore, the post 176 and finger pad 174 extend out of the cavity 162 when the retraction trigger 170 is pivotably mounted within the cavity 160, for purposes which will become apparent hereinafter.

With reference again to FIG. 22, the deploying lever 168 has a pair of leg extensions 184, 186 with holes 188, 190 for receiving therethrough a pin 192 which extends from the retraction trigger 170, whereby the deploying lever 168 is pivotably mounted onto the retraction trigger 170. As shown in FIGS. 17 and 19–21, the deploying lever 168 also has a thumb peg 194 which extends out of the cavity 162 and with which the deploying lever 168 is movable between an undeployed position (see FIG. 17) and a deployed position (see FIG. 19), as will be described hereinafter.

With reference to FIGS. 17–20 and 22, the handle 154 also includes a hollow shaft 196 extending therefrom and having a through passage 198. The device 152 further includes a hollow sleeve 200 that is connected to and extends from the hollow shaft 196 of the handle 154. The hollow sleeve 200 has a through passage 202 (see FIG. 22 only), as well as a proximal portion 204 and a distal portion 206 that is narrower than the proximal portion 204. An actuator sleeve 208 is slideably received within the through passages 198, 202 of the hollow shaft 196 and the hollow sleeve 200. The actuator sleeve 208 has a fork extension 210 at its proximal end that is sized and shaped to be moveably attached to the thumb peg 194 of the deploying lever 168 (see FIGS. 17, 19 and 20). The actuator sleeve 208 also has a pair of prongs 212, 214, each with a hole 216, 218, respectively, at its distal end, for a purpose which will be explained hereinafter.

With continued reference to FIGS. 17–20 and 22, the actuator sleeve 208 has a bore 220 (shown in phantom in FIG. 22 only) therethrough within which a retraction rod 222 is slideably received. The proximal end of the retraction rod 222 is provided with a connector 224 having a hole 226 which is sized and shaped to receive the post 176 of the retraction trigger 170 therethrough, in a moveable manner (see FIGS. 17–20). The retraction rod 222 also has, at its distal end, a tab 228 with a hole 230 and a pin 232, for a purpose which will be explained hereinafter.

The device 152 also includes a cylindrical transducer 10d that is securely received about the narrow distal portion 206 of the hollow sleeve 200. In addition, a first hemi-cylindrical transducer 22g is mounted onto a first carrier bar 234. The first carrier bar 234 has a tongue 236 at one end with a first hole 238 proximate to the first carrier bar 234 and a second hole 240 located remotely from the first carrier bar 234. The second hole 240 of the first carrier bar 234 is aligned with the hole 230 on the tab 228 at the distal end of the retraction rod 222 and a plug 242 is inserted through both holes 230, 238, thereby moveably attaching the first carrier bar 234 to the retraction rod 222 (see dotted lines in FIG. 22 and see FIG. 23). The first carrier bar 234 is moveably connected to the distal end of the actuator sleeve 208 by a first connector rod 244 having two hooked ends 246, 248, as follows. As indicated by the dotted lines provided in FIG. 22 and shown in FIG. 23, one hooked end 246 of the first connector rod 244 is pivotably inserted into the hole 216 of one of the prongs 212 at the distal end of the actuator sleeve 208 and the other hooked end 248 is pivotably inserted into the first hole 238 on the tongue 236 of the first carrier bar 234.

The device 152 also includes a second hemi-cylindrical transducer 22g mounted onto a second carrier bar 250. The second bar carrier bar 250 has a tongue 252 at one end with a first hole 254 proximate to the second carrier bar 250 and a second hole 256 located remotely from the second carrier bar 250. The pin 232 on the tab 228 at the distal end of the retraction rod 222 is moveably received within the second hole 256 of the second carrier bar 250, thereby moveably attaching the second carrier bar 250 to the retraction rod 222 (see dotted lines in FIG. 22 and see FIG. 23). The second carrier bar 250 is moveably connected to the distal end of the actuator sleeve 208 by a second connector rod 258 having two hooked ends 260, 262, as follows. As indicated by the dotted lines provided in FIG. 22 and shown in FIG. 23, one hooked end 260 of the second connector rod 258 is pivotably inserted into the hole 218 of the other prong 214 at the distal end of the actuator sleeve 208 and the other hooked end 262 of the second connector rod 258 is pivotably inserted into the first hole 254 on the tongue 252 of the second carrier bar 250.

It is noted that, although not specifically shown in the figures, the cylindrical transducer 10d and the hemi-cylindrical transducers 22g, 22h each have a pair of electrically conductive wires (not shown), preferably as a coaxial cable (not shown), that are connected to their inner and outer surfaces, as well as to one or more RF power sources (not shown), as described hereinabove in connection with the construction and operation of the cylindrical and hemi-cylindrical transducers 10, 22. To protect the wires and minimize interference with the manipulation and operation of the device 152 by the surgeon, the aforesaid wires (not shown) can be attached to the cylindrical transducer 10d and the hemi-cylindrical transducers 22g, 22h and extended through the through passages 198, 202 of the hollow shaft 196 and hollow sleeve 200 (or through the bore 220 of the actuator sleeve 208), to the RF power source (not shown).

In the foregoing arrangement, during operation of the device 152, when RF power is supplied to the transducers 10d, 22g, 22h, ultrasound energy is emitted by the cylindrical transducer 10d in a radially outward direction, as discussed hereinabove in connection with the typical cylindrical transducer 10. Furthermore, when the device 152 is in its deployed state (see FIGS. 19 and 20), the carrier bars 234, 250 and also, therefore, the hemi-cylindrical transducers 22g, 22h mounted thereon, are oriented perpendicularly to the cylindrical transducer 10d and ultrasound energy is emitted by the hemi-cylindrical transducers 22g, 22h in the direction shown by the arrows in FIG. 21 (which shows the device 152 in use, in its deployed state, after insertion into the vagina 100" and uterus 98" of a female patient). The method of operating the device 152 in accordance with the present invention, as well as the advantages achieved thereby, will be described in further detail hereinafter.

With reference now to FIGS. 17, 19 and 20, operation of the device to move the hemi-cylindrical transducers 22g, 22h from their undeployed positions to their deployed and retracted positions will now be explained. It is noted that the cylindrical transducer 10d is not deployable and, therefore, remains in a fixed position with respect to the hollow sleeve 200. With reference in particular to FIG. 17, the device 152 is shown with the hemi-cylindrical transducers 22g, 22h in their undeployed and extended positions and, when they are in such positions, the retraction lever 170 of the handle 154 is positioned such that the finger pad 174 extends fully out of the cavity 162 and the post 176 is at a position nearest to the hollow shaft 196. In addition, the deploying lever 168 is pivoted away from the retraction lever 170 such that the thumb peg 194 is pivoted to a position away from the post 176.

When the thumb peg 194 is pressed (for example, by a surgeon's thumb) toward the post 176 and hollow shaft 196, in the direction indicated by the arrow F in FIG. 19, the actuator sleeve 208 is moved slideably through the through passages 198, 202 of the hollow shaft 196 and the hollow sleeve 200, respectively, in the direction indicated by the arrow G in FIG. 19. The distal end of the actuator sleeve 208, in turn, pushes the first and second connector rods 244, 258 also in the direction of the arrow G in FIG. 19. The retractor rod 222 remains stationary and, as a result of the movement of the first and second connector rods 244, 258, the first and second carrier bars 234, 250 (with the hemi-cylindrical transducers 22g, 22h mounted thereon) are pivotably moved (in the directions indicated by the arrows H in FIGS. 17 and 19) from their undeployed positions (see FIG. 17) to their deployed positions (see FIGS. 19 and 20), which is perpendicular to the cylindrical transducer 10d and the hollow sleeve 200.

As shown in FIG. 19, when the first and second carrier bars 234, 250 (with the hemi-cylindrical transducers 22g, 22h mounted thereon) are pivotably moved to their deployed positions, the distance between the hemi-cylindrical transducers 22g, 22h and the cylindrical transducer 10d become significant. Thus, it is preferable to move, or retract, the hemi-cylindrical transducers 22g, 22h closer to the cylindrical transducer 10*d* and hollow sleeve 200 (i.e., in the direction indicated by the arrow J in FIG. 20).

Thus, when the finger pad 174 is pushed into the cavity 162 of the handle 154 (in the direction indicated by the arrow K in FIG. 20), the entire retraction lever 170 is pivoted backward, which moves the post 176 and the thumb peg 194 (with the actuator sleeve 208 connected thereto) backward away from the hollow shaft 196 (in the direction indicated by the arrow L in FIG. 20). The actuator sleeve 208 is moved slideably backward though the through passages 198, 202 of the hollow shaft 196 and the hollow sleeve 200, respectively, in the direction indicated by the arrow J in FIG. 20). Similarly and simultaneously, the retraction rod 222 is also slideably moved in the direction indicated by the arrow J in FIG. 20, through the bore 220 of the actuator sleeve 208, which pulls, or retracts, the first and second carrier bars 234, 250 (with the hemi-cylindrical transducers 22*g*, 22*h* mounted thereon), in their deployed positions, backward toward the cylindrical transducer 10*d* and hollow sleeve 200, in the direction of the arrow J. After the foregoing procedure, the device 154 and hemi-cylindrical transducers 22*g*, 22*h* are in their deployed positions, which are shown in FIG. 20.

With reference to the overall size and shape of the device 152, the sum of the lengths of the hollow shaft 196 and hollow sleeve 200 should be between about 10 and 30 cm, preferably about 20 cm. Regarding the individual lengths of these components, the length of the hollow shaft 196 should be from about 5 to 10 cm, preferably about 10 cm, and the length of the hollow sleeve 200 should be from about 5 to 15 cm, preferably 10 cm. Moreover, the outer diameters of the hollow shaft 196 and the proximal portion 204 of the hollow sleeve 200 should be substantially the same as one another and, more specifically, from approximately 3 to 10 mm, preferably about 5 mm. The outer diameter of the narrow distal portion 206 of the hollow sleeve 200 should correspond to the inner diameter of the cylindrical transducer 10*d* such that the cylindrical transducer 10*d* is snugly received thereon. Furthermore, the length of the narrow distal portion 206 of the hollow sleeve 200 should be the same or slightly (i.e., about 2 to 5 mm) longer than the length of the cylindrical transducer 10*d*, which is specified hereinafter.

The diameter of the through passages 198, 202 of the hollow shaft 196 and the hollow sleeve 200, respectively, should be large enough to slidingly receive therethrough the actuator sleeve 208 all of the wires (not shown) attached to the cylindrical transducer 10*a* and the incomplete cylindrical transducers 10*b*, 10*c*, more particularly, from about 3 mm to 10 mm, preferably about 4 mm. In addition, the length of the first and second carrier bars 234, 250 should, but do not have to be, approximately the same as one another, for example, between about 10 and 3 mm long each, preferably about 15 mm long each.

With regard to the size of the cylindrical transducer 10*d* and the hemi-cylindrical transducers 22*g*, 22*h*, it is noted that, although they are shown in FIGS. 17–22 as being of the same general size as one another, they do not have to be the same size and, in fact, may be differently sized. It is preferable, however, that the two hemi-cylindrical transducers 22*g*, 22*h* be of similar size and shape to one another. In the present embodiment of the device 152, each of the transducers 10*d*, 22*g*, 22*h* is between about 1 and 3 cm long, preferably about 1.5 cm long. Moreover, a suitable diameter for the cylindrical transducer 10*d* is about 5 to 10 mm in diameter, preferably about 5 mm in diameter. In addition, each hemi-cylindrical transducer 22*g*, 22*h* is about 5 to 10 millimeters (mm) wide at its greater width such that, when the hemi-cylindrical transducers 22*g*, 22*h* are in the undeployed state, they approximate the shape of a cylindrical transducer having an overall diameter of about 5 to 10 mm, preferably about 5 mm.

The method of operating the device 152 of the second embodiment to perform endometrial ablation will now be described. Initially, it is noted that, like the devices 34, 108 of the first and second embodiments discussed hereinabove, the device 152 of the second embodiment may be used in conjunction with a fluid-filled balloon, such as is well-known in the art for treating the endometrium, or it may be used without such a balloon and, instead the uterus should be filled with fluid.

With reference now to FIG. 21, after the uterus 98" has been prepared and filled with fluid, as described hereinabove, the device 152 in its undeployed state (see FIGS. 10 and 11) is inserted into the uterus 98" of a patient. More particularly, the device 152 is held by the handle 154 by the surgeon and the first and second carrier bars 234, 250 (with the undeployed hemi-cylindrical transducers 22*g*, 22*h* mounted thereon), the cylindrical transducer 10*d*, and at least a portion of the hollow sleeve 200 are inserted through the vagina 100" and into the uterus 98". The transducers 10*d*, 22*g*, 22*h* are positioned approximately centrally within the uterus 98", or at an otherwise appropriate position within the uterus 98" as clinically determined by the surgeon. The hemi-cylindrical transducers 22*g*, 22*h* are then deployed and retracted, as described above in connection with FIGS. 17, 19 and 20, by first pressing the thumb peg 194 in the direction indicated by the arrow F in FIG. 19 to deploy the hemi-cylindrical transducers 22*g*, 22*h* into a position that is perpendicular to the cylindrical transducer 10*d*. Then the finger peg 174 is in the direction of the arrow K in FIG. 20 to retract the hemi-cylindrical transducers 22*g*, 22*h* into a position that is closer to the cylindrical transducer 10*d*.

The RF power source (not shown) is then turned on, which causes RF power to be delivered to the transducers 10*d*, 22*g*, 22*h*, which causes them to emit ultrasound energy, as shown by the arrows in FIG. 21, that travels to the endometrium 106" where it is absorbed, resulting in heating and ablation of the endometrial tissue. After a period of time, which is clinically determined by the surgeon, the RF power source (not shown) is turned off, which ceases the ultrasound energy emissions from the transducers 10*d*, 22*g*, 22*h*. Typically, the period of time between turning the RF power source on and turning it off is between about 2 and 10 minutes, but no more than about 20 minutes and preferably from about 2 to 3 minutes.

As can be seen from viewing FIG. 21, the ultrasound energy emitted by the transducers 10*a*, 10*b*, 10*c* when the device 152 is in its deployed state achieves wider coverage of the endometrium 106" than the ultrasound energy that would be emitted from a device having only longitudinally aligned transducers (such as, for example, the arrangement of the transducers 10*d*, 22*g*, 22*h* when the device 152 is in its undeployed state as in FIG. 17). More particularly, in its deployed state, the device 154 delivers ultrasound energy directly to the top wall 150" of the uterus 98", which would otherwise be nearly entirely neglected by existing devices having only longitudinally aligned transducers. As with the devices 34, 108 of the first and second embodiments, the device 152 of the third embodiment can be moved, for example back and forth or tilted, during in situ use such that the transducers 10*d*, 22*g*, 22*h* are also so moved within the uterus 98" of the patient. Such movement will allow the surgeon to have greater directional control of at least a portion of the ultrasound energy that is emitted from the transducers 10d, 22g, 22h toward the endometrial tissue. The RF source may have multiple (for example, three) individual channels such that the power level supplied to each of the transducers 10d, 22g, 22h can be individually controlled. The transducers 10d, 22g, 22h may also be "multiplexed" such that a single RF power source is sequentially switched among the transducers 10d, 22g, 22h.

It will be understood that the embodiments described herein are merely exemplary and that a person skilled in the art may make many variations and modifications, including but not limited to those discussed hereinabove, without departing from the spirit and scope of the present invention. All such variations and modifications are intended to be included within the scope of the invention as defined in the appended claims.

We claim:

1. A device for thermal ablation therapy, comprising emitting means for emitting ultrasound energy capable of heating tissue, said emitting means being movable between an undeployed position, in which said emitting means is in a first orientation which facilitates insertion of said device, and a deployed position, in which said emitting means is in a second orientation, which is different from said first position, said second orientation being selected to efficiently deliver ultrasound energy to tissue to be ablated, said emitting means being movable from its said undeployed position to any one of an infinite number of orientations for efficiently delivering ultrasound energy to tissue to be ablated, said emitting means including at least one piezoelectric transducer securely mounted to said carrier; and moving means for moving said emitting means between its said undeployed and deployed positions, said moving means including a movable carrier, said emitting means being mounted on said carrier for conjoint movement therewith, said moving means including a rod which has a distal end and a proximal end, and a hollow sleeve, which has a through passage, said rod being slideably received in said through passage, said distal end of said rod being connected to said carrier for moving said at least one piezoelectric transducer between its said undeployed position and its said deployed position in response to sliding movement of said rod.

2. The device according to claim 1, wherein said at least one piezoelectric transducer and said sleeve are arranged relative to each other in a linear manner when said at least one piezoelectric transducer is in its said undeployed position and said at least one piezoelectric transducer and said sleeve are arranged relative to each other in a non-linear manner when said at least one piezoelectric transducer is in its said deployed position.

3. The device according to claim 2, wherein said moving means includes a handle having a movable part, said movable part being connected to said proximal end of said rod for moving said at least one piezoelectric transducer between its said undeployed position and its said deployed position in response to movement of said movable part of said handle.

4. The device according to claim 3, wherein said at least one carrier includes a first carrier, said at least one piezoelectric transducer includes a set of first transducers mounted linearly on said first carrier; and wherein said at least one carrier includes a second carrier, said at least one piezoelectric transducer includes a set of second transducers mounted linearly on said second carrier.

5. The device according to claim 4, wherein said first transducers are arranged linearly relative to said sleeve and said second transducers are arranged linearly relative to said sleeve when said first and second transducers are in said undeployed position, whereby said first transducers are substantially parallel relative to said second transducers.

6. The device according to claim 5, wherein said first transducers are arranged at an angle relative to said sleeve and said second transducers are arranged at an angle relative to said sleeve when said first and second transducers are in said deployed position, whereby said first transducers are positioned at an angle relative to said second transducers.

7. The device according to claim 6, wherein each of said first and second transducers has a hemi-cylindrical shape and includes an arcuate surface, said arcuate surfaces of said first transducers and said arcuate surfaces of said second transducers are oriented in substantially opposite directions such that energy emitted from said first and second transducers travels outwardly from said arcuate surfaces with minimal overlap.

8. The device according to claim 7, wherein said rod includes a first rod, which is connected to said first carrier, and a second rod, which is connected to said second carrier, said first and second rods being connected to said movable part of said handle.

9. The device according to claim 3, wherein said at least one transducer includes a plurality of transducers mounted linearly on said at least one carrier.

10. The device according to claim 9, wherein said transducers are arranged linearly relative to said sleeve when said transducers are in said undeployed position; and wherein said transducers are arranged perpendicularly relative to said sleeve when said transducers are in said deployed position.

11. The device according to claim 10, wherein each of said transducers has a substantially cylindrical outer surface such that energy emitted from said transducers travels radially outwardly from said transducers.

12. The device according to claim 11, further comprising a stationary piezoelectric transducer immovably mounted to said sleeve, said stationary piezoelectric transducer having a substantially cylindrical shape and being arranged linearly in relation to said sleeve.

13. The device according to claim 3, wherein said at least one carrier includes a first carrier, said at least one piezoelectric transducer including a first transducer mounted on said first carrier; and wherein said at least one carrier includes a second carrier, said at least one piezoelectric transducer including a second transducer mounted on said second carrier, said first and second carriers being pivotable relative to one another such that said first and second transducers are movable between said undeployed and deployed positions.

14. The device according to claim 13, wherein said first transducer is arranged linearly relative to said sleeve and said second transducer is arranged linearly relative to said sleeve when said first and second transducers are in said undeployed position, whereby said first transducer is positioned substantially parallel relative to said second transducer.

15. The device according to claim 14, wherein said first transducer is oriented substantially perpendicularly relative to said sleeve and said second transducer is oriented substantially perpendicularly relative to said sleeve when said first and second transducers are in said deployed position, whereby said first transducer and said second transducer are arranged linearly relative to one another.

16. The device according to claim 15, wherein each of said first and second transducers has a hemi-cylindrical shape and includes an arcuate surface, said arcuate surfaces of said first transducers and said arcuate surfaces of said second transducers are oriented in substantially the same direction when said first and second transducers are in said deployed positions, such that energy emitted from said first and second transducers travels outwardly from said arcuate surfaces with minimal overlap.

* * * * *